United States Patent [19]
Russell

[11] Patent Number: 5,481,265
[45] Date of Patent: Jan. 2, 1996

[54] ERGONOMIC CUSTOMIZEABLE USER/COMPUTER INTERFACE DEVICES

[76] Inventor: David C. Russell, 2967 Aldgate Dr., Bloomfield Hill, Mich. 48013

[21] Appl. No.: 879,374

[22] Filed: May 7, 1992

Related U.S. Application Data

[63] Continuation-in-part of Ser. No. 440,771, Nov. 22, 1989, abandoned.

[51] Int. Cl.$^6$ ................................................ G06F 3/033
[52] U.S. Cl. .......................... 341/22; 341/21; 341/23; 345/157; 345/169; 345/172; 340/825.31
[58] Field of Search .................................. 341/20, 21, 23; 345/156–158, 169, 172; 364/706, 709.05, 709.1; 340/825.19, 825.69, 825.72, 825.31, 825.34, 825.56

[56] References Cited

U.S. PATENT DOCUMENTS

| | | |
|---|---|---|
| 4,337,483 | 6/1982 | Guillou . |
| 4,453,161 | 6/1984 | Lemelson . |
| 4,458,238 | 7/1984 | Learn . |
| 4,578,674 | 3/1986 | Baker et al. . |
| 4,628,541 | 12/1986 | Beaver . |
| 4,641,374 | 2/1987 | Oyama . |
| 4,654,648 | 3/1987 | Herrington et al. . |
| 4,682,159 | 7/1987 | Davison . |
| 4,754,268 | 6/1988 | Mori . |
| 4,763,291 | 8/1988 | Schwaber . |
| 4,763,993 | 8/1988 | Vogeley et al. . |
| 4,808,995 | 2/1989 | Clark et al. ................ 340/825.31 |
| 4,812,842 | 3/1989 | Bayerlein et al. . |
| 4,823,311 | 4/1989 | Hunter et al. .................. 345/172 |
| 4,844,475 | 7/1989 | Saffer et al. . |
| 4,853,682 | 8/1989 | Asano et al. . |
| 4,897,820 | 1/1990 | Thierry et al. . |
| 4,905,001 | 2/1990 | Penner . |
| 4,922,236 | 5/1990 | Heady . |
| 4,924,216 | 5/1990 | Leung . |
| 4,951,249 | 8/1990 | McClung et al. . |
| 4,954,817 | 9/1990 | Levine . |
| 4,961,224 | 10/1990 | Yung . |
| 4,988,981 | 1/1991 | Zimmerman et al. . |
| 5,018,096 | 5/1991 | Aoyama . |

FOREIGN PATENT DOCUMENTS

| | | |
|---|---|---|
| 59-174938 | 10/1984 | Japan . |
| 60-225910 | 11/1985 | Japan . |

Primary Examiner—Michael Horabik
Attorney, Agent, or Firm—Dickstein, Shapiro & Morin

[57] ABSTRACT

A ergonomic customizeable user/computer interface system for wireless computer control. A hand-attachable user interface device transmits control information upon activation of switches on the interface device. A base interface device receives the transmissions, decodes the information and provides control signals to the computer. The interface system allows for security authorization control and multiple computer or LAN operations with each user interface device. Greater functionality is provided by the use of personality modules in the user interface device for different modes of operation.

41 Claims, 22 Drawing Sheets

FIG. 1B
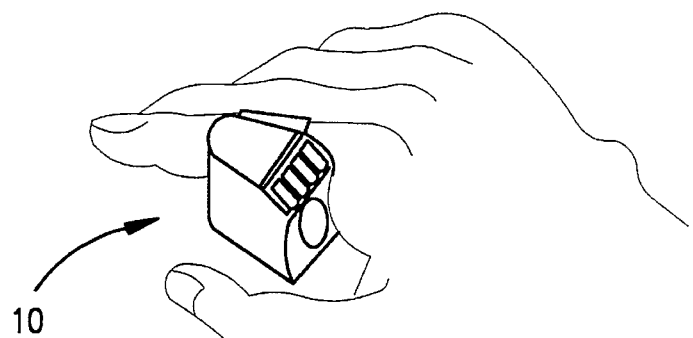
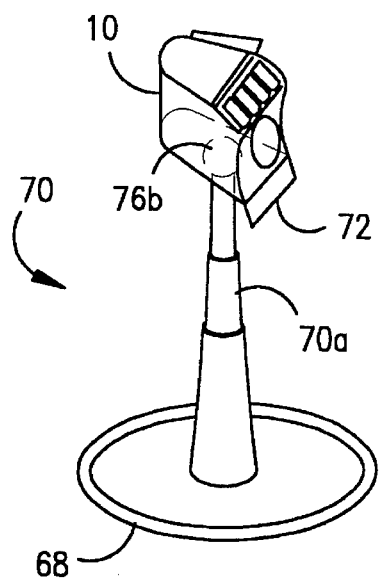
FIG. 1C
FIG. 1D
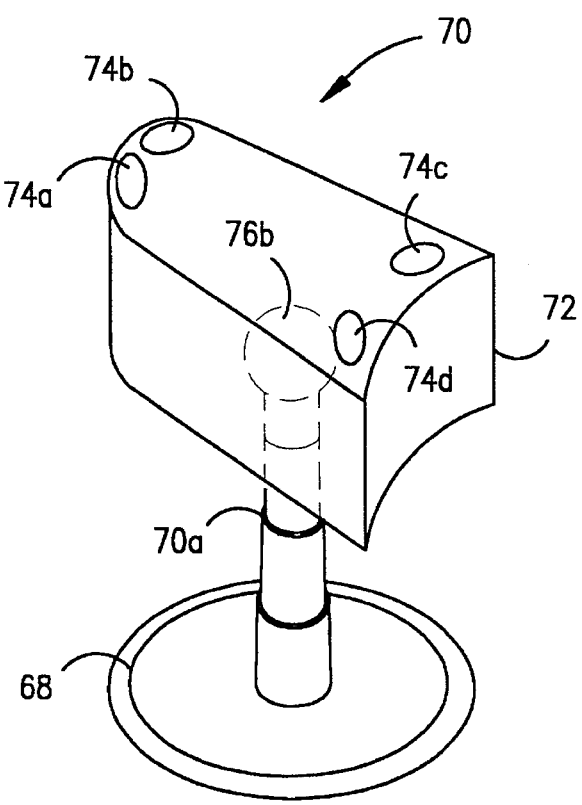

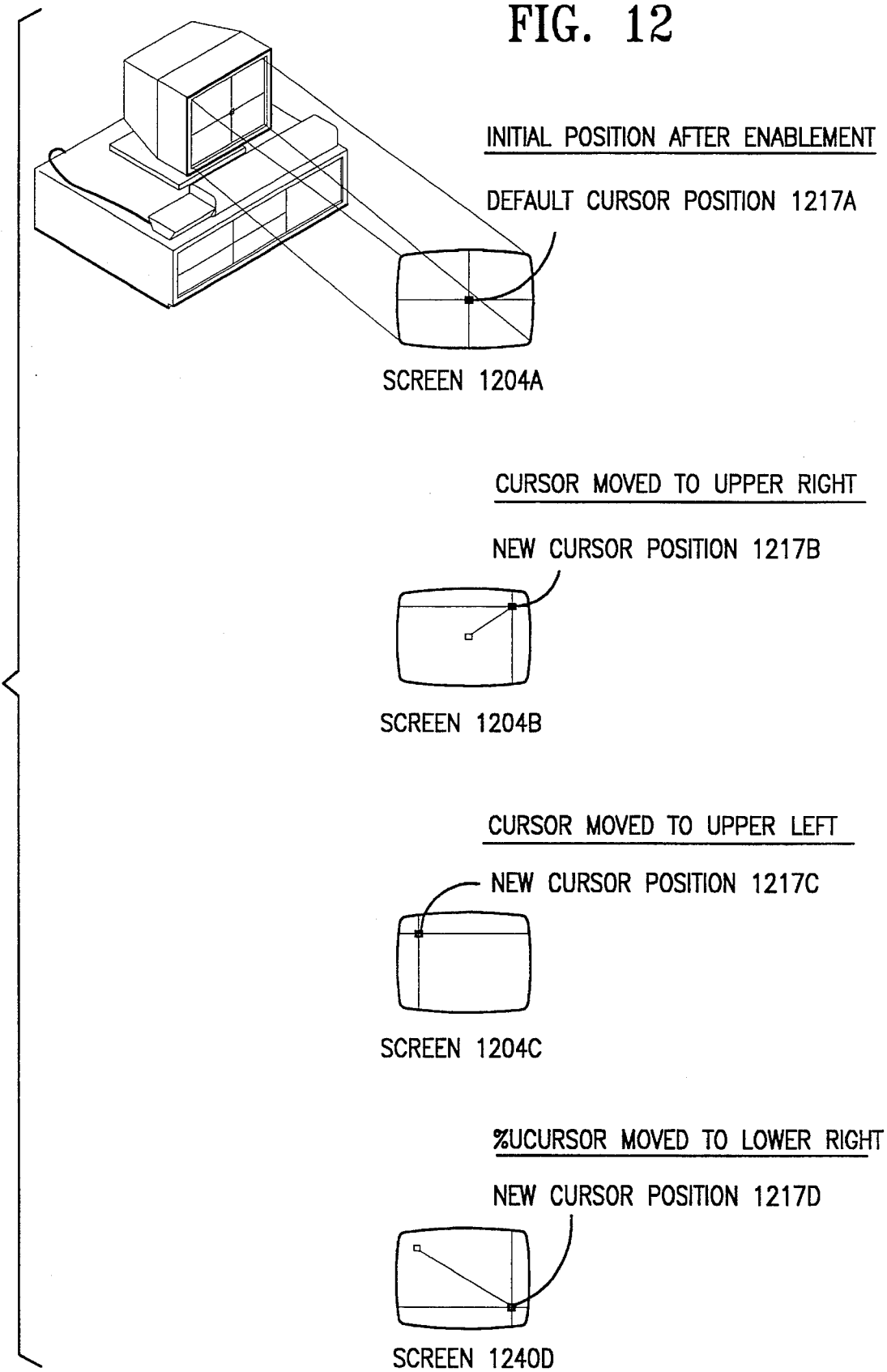

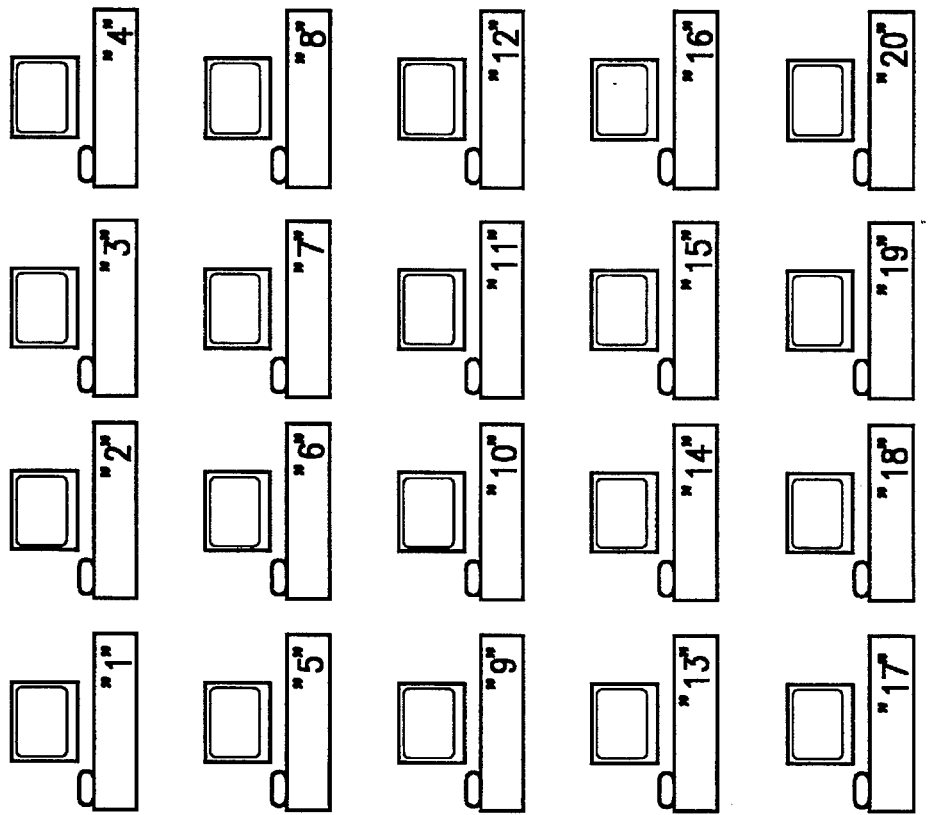

FIG. 16C.1

SYSTEM AND GENERAL RUNDOWN

| FIELD 1 | FIELD 2 | FIELD 3 | FIELD 4 | FIELD 5 | FIELD 6 |
|---|---|---|---|---|---|
| FLAG | DEVICE ID FIELD | DEVICE GROUP ID FIELD | USER ID FIELD | USER CONTROL SIGNAL (FUNCTION 1.01) | MESSAGE STOP FLAG FIELD |

FIG. 16C.2

CURSOR MOVEMENT AND RELATED

| FIELD 1 | FIELD 2 | FIELD 3 | FIELD 4 | FIELD 5 | FIELD 6 | FIELD 7 |
|---|---|---|---|---|---|---|
| FLAG | DEVICE ID | DEVICE GROUP ID | USER ID FIELD | NODE | (FUNCTION 2.01) | STOP FLAG |

FIG. 16C.3

SELECTION AND RELATED

| FIELD 1 | FIELD 2 | FIELD 3 | FIELD 4 | FIELD 5 | FIELD 6 | FIELD 7 |
|---|---|---|---|---|---|---|
| FLAG | DEVICE ID | DEVICE GROUP ID | USER ID FIELD | NODE | (FUNCTION 3.01) | STOP FLAG |

FIG. 16C.4

SECONDARY SWITCH COMMANDS

| FIELD 1 | FIELD 2 | FIELD 3 | FIELD 4 | FIELD 5 | FIELD 6 | FIELD 7 |
|---|---|---|---|---|---|---|
| FLAG | DEVICE ID | DEVICE GROUP ID | USER ID FIELD | NODE | (FUNCTION 4.01) | STOP FLAG |

ERGONOMIC CUSTOMIZEABLE USER/COMPUTER INTERFACE DEVICES

This is a continuation in part of application Ser. No. 07/440,771, filed Nov. 22, 1989, now abandoned.

BACKGROUND OF THE INVENTION

FIELD OF THE INVENTION

The present invention relates to user/computer interface devices, specifically with respect to graphical interfaces. More specifically, the present invention relates to wireless transmissions from an ergonomic remote control device to a base device for control of computer functions and applications.

DESCRIPTION OF THE ART

In recent years, the process of entering certain types of data and control inputs into computer based systems has been significantly simplified. Traditionally, data entry to a computer has been done with a standard computer keyboard. However, for many users, the keyboard proved to be insufficiently mobile and accessible, inconvenient, and time consuming.

The user/computer interface has been simplified by "graphic user interfaces" (GUIs) and "pointing devices." The user can select an icon from a GUI display to activate the predetermined function or event associated with the icon.

Since GUIs first emerged, alternatives to the keyboard have proven highly desirable for optimum productivity in many applications. Accordingly, auxiliary or keyboard alternative hardware such as light pens, joysticks, trackballs, touch pads, digitizing pads, and the "computer mouse" developed. These new GUI-oriented pointing devices quickly proved to be viable, timesaving alternatives to the keyboard for many types of computer input and control situations. In particular, the mouse has become the single most widely-accepted keyboard alternative input device.

The fundamental operating principle of the mouse relates to the rotation of a spherical trackball carried within the mouse. When the mouse is moved over a flat surface, the trackball, which is partially exposed, freely rotates within the device and generates signals which correspond to pairs of x-axis and y-axis coordinates. The mouse contains means to translate these coordinates into signals to which the attached computer is responsive. Accordingly, when the computer user moves the mouse device across a working surface adjacent to the computer, the cursor indicator on the display screen moves to the location pointed to by the computer user. Also, the computer user's operation of one or more buttons aboard the mouse effects other control functions of the computer and computer display, such as the selection of computer usage event options.

Notwithstanding the contributions of mouse products and other alternative input devices, many computer input and control needs remain unmet by the prior art. The mouse requires a prominent, smooth, flat, horizontal space on the user's desk. In practice, a typical user's desk is crowded and inhibits the space required for mouse operation. Most mouse devices are especially difficult to use when away from traditional office facilities, in mobile or restricted locations.

Users who operate their computers while travelling, or who operate computers in non-office situations find few computer input products that specifically address the needs of laptop and notebook computing. Some mouse type devices have been developed for mobile users. However, the computer user must make special adjustments to clamp-on fittings to attach these products to the computer keyboard. Some of these products must first be physically clamped onto the computer for each work session, then must be physically unclamped, when the work session is over. Also, the computer user must move his/her hand back and forth from keyboard to the clamp-on product to operate it. Another main complaint made by many users and industry analysts is that users' thumbs quickly tire, operating the small trackballs provided on these products.

One drawback of the mouse results from hardwired attachment to the computer. The connecting cord from the mouse to the computer is subject to the same "umbilical" problems associated with cords on any appliance which needs to move about, to operate according to design. Some wireless computer input devices exist, but their need for dedicated horizontal surfaces precludes many potential benefits of wirelessness.

Users with physical impairments often find mouse products difficult to operate. Depending on the physical impairment, both mouse and keyboard computing can be difficult, painful, or impossible for impaired users. For users with arthritis, carpal tunnel syndrome, or tendonitis, mouse usage can be an awkward and painful. There is a recognized need for GUI devices which offer prophylaxis for users with physical impairments and repetitive stress injuries. While successful products serve a variety of needs for these users, high costs and highly specific utility of many such products hinder their widespread acceptance.

Technicians and professionals often have advanced or high-functionality needs. Many of these specialized needs are unmet by traditional desktop mouse-type products, or by products such as the aforementioned mobile computer input products. High costs and highly-specific utility of many such high functionality products also hinder their widespread use.

Another mouse drawback is its' simplex, unidirectional design and operation. No mouse currently implements two-way interaction between controlled computers and input devices. Lack of bidirectionality is better appreciated, if one considers the many new applications and benefits of bidirectionality, such as roaming LAN interaction; security and alarms; mobile signaling and paging; and remote interactive applications.

Computer users have local area network (LAN) and security needs which remain unmet by current input devices. LAN users have connectivity needs which extend beyond their own computer. LANs were created to facilitate resource-sharing of limited resources among multiple users. LAN users often access and connect into one or more LANs, or other accessible computers or network environments. It has been estimated that more than half of all computers in business are attached to a LAN.

In addition, as the computer population grows, security grows more important. Computers increasingly store confidential data, and no mouse products are designed or equipped for individually-assignable security to add to a computing installations' security "shield".

No shortage of LAN products or security products exist. However, no security-oriented, individually-assignable computer input and control products are available which allow LAN users to conveniently transport and securely operate personal GUI-oriented pointing devices in multiple LAN locations. "Security-oriented users" need to limit access to critical resources, including hardware, software, data and information, networks, etc. As LANs become more widespread, security becomes much more important, to ensure privacy.

The underside of the mouse trackball is susceptible to the introduction of dirt, liquids, or other substances into the body cavity. This vulnerability can lead to equipment failure and shorter product life.

Another drawback of the mouse is that the user may find the "mouse method" of frequently moving his or her hand back and forth from the keyboard to the mouse to be distracting to their train of thought, time consuming, or inconvenient to optimal operational efficiency.

Several inventors have attempted to address some of these aforementioned drawbacks and problems.

For example, U.S. Pat. No. 4,550,250 to Mueller discloses an infrared graphic input device for a computer. A remote infrared light source transmits user input commands to a detector device adjacent to the computer. The device must operate within a dedicated horizontal, two-dimensional, smooth, flat surface. The detector apparatus operates according to continuous tracking input principles and does not allow for any straying out of equipment detection boundaries.

U.S. Pat. No. 4,578,674 discloses a method and an apparatus for controlling the cursor position on a computer display screen. This device uses both infrared and ultrasonic principles for determining the direction and the velocity of motion of a positioning device which is monitored by a control base detector. The device requires a two-dimensional plane. To operate from a three-dimensionally defined location, the user must ensure the emitter/detector front face of the positioning device is always directly facing the control base.

U.S. Pat. No. 4,628,541 to Beavers discloses an infrared battery powered keyboard input device for a microcomputer. This device offers the user additional freedom for operating a standard style keyboard without hardwiring constraints. Also, the keyboard cannot be portable to another computer, unless the computer to which the keyboard is ported is a "mirror" microcomputer device. Apparently, the infrared battery operated keyboard likely requires the implementation of a separate mouse if "mouse-type" input commands or functionality/features are needed by the user or are required for optimal productivity.

SUMMARY OF THE INVENTION

In view of the foregoing, it is apparent that there still exists a need in the art for a method, apparatus, system, and architecture which provides a more efficient and effective means to easily and conveniently accomplish user/computer interface. The present invention addresses and solves many or all of the aforementioned drawbacks, for many usage-specific applications and environmental contexts.

Accordingly, the invention herein disclosed offers many distinct and unique capabilities, to serve a wide range of user needs. The present invention can simplify access to computers, and can accelerate user and computer interaction-especially for GUI user/computer applications, and for mobile operating environments. The present invention eliminates or reduces many drawbacks of many existing input devices and mouse-type products.

The invention relates to a method to improve computer accessibility, by simplifying user and computer interaction. The apparatus of the present invention can provide very easy access to, and control of, graphic user interface-oriented computing environments, particularly for persons with mobility impairments and for persons with special mobility requirements. A mobile, lightweight, ergonomically-shaped, customizeable, user/computer interface apparatus is attached onto the human forefinger, providing means for thumbtip interaction with a computer, via predetermined user control signals. To couple user control signals from the user-attachable apparatus to a controllable computer, a hard-wired or wireless signal transmission system receives user control signals and relays them to a base/computer interface apparatus, which detects, decodes, and converts user control signals into formats suitable for input to and processing by an interconnected controllable computer. In one preferred embodiment, computer-generated or other external control signals can disable operation of a base/computer interface apparatus and a user/computer interface apparatus, when necessary for security.

The system and architecture of the invention provides networking of multiple user/computer and base/computer interface devices and other interface device combinations, as means for controlling multiple controllable computers, over at least one computer network.

Using the present invention, the computer user can control any controllable computer event remotely, without the need for a dedicated, cleared, smooth, flat, horizontal, desktop surface or typical office facilities. Not requiring restrictive, immediate proximity to the controlled computer is a cardinal benefit of this invention and several preferred embodiments.

An object of the present invention is to provide a cordless, user/computer interface device operable from any three dimensional location sufficiently proximate to the base transceiver for signals to reach it.

Another object of the invention is to provide a computer input device which is operable from any location reasonably close to the computer being controlled, and which does not require a prominent, dedicated, cleared, smooth, flat, horizontal surface or other special surface upon which to run.

Another object of this invention is to provide an ergonomically shaped and ergonomically operable device to serve needs of users with physical impairments or handicaps. It is therefore an object of the present invention to provide a wireless GUI-oriented user/computer interface device which is easily attachable to the user's index finger, which can be comfortably "worn" for extended periods of time, and which can be very easily operated by thumbtip and/or forefinger pressure. A further related object is to provide a GUI-oriented user/computer interface device, operable without the need to move the user's hands away from the computer keyboard.

It is an object of the invention to provide a device not susceptible to dirt, liquids, or other foreign substances which can be introduced through its' underbody, by eliminating the trackball and aperture, with a "contrarian" product design.

Another object is to provide a security option for GUI applications. Given bidirectional functionality of this invention, secured two-way authentication sequences can be used to control LANs, enterprise-wide networks, other network resources, other computing resources, and other controllable machinery.

A related object is to provide a secure, mobile, highly flexible GUI equipment design which allows the user to carry his or her own user/computer interface device from one location to another or from a desktop computer to a notebook or laptop computer, with equal facility.

Another object is to provide a highly flexible, customizeable GUI equipment design, which can provide multiple basic "personality operating environment" options, using multiple, different "personality modules" (i.e., different ROMs) which can be swapped in and out of device 10, depending on user selection of the needed "personality module".

Another object of the invention is to provide an easy-to-use method for operating GUI software.

Another object is to provide a user/computer interface system with very sensitive signal radiating and sensing means, allowing signal transmission and reception without rigorous aiming of the input device.

Another object is to provide a user/computer interface architecture which can be configured to provide for an interoperable computing environment, wherein a group or groups of computers can be controlled by one or more authorized users and authorized user/computer interface devices, depending on user and interface device privileges. A related object of this invention is to provide a control unit for an enterprise-wide computer security system.

Another primary object of the present invention is to provide computer input and control with a device which is externally switchless, in one preferred embodiment.

It is another object of the present invention to provide a method for flexible computer control using wireless signal transmissions.

Briefly described, these and other objects of the invention are accomplished with its' method, apparatus, system, and architecture aspects by providing a wireless user/computer interface device adapted to communicate with a base/computer interface device, which is interconnected into a controllable computer equipped with driver software of the present invention.

BRIEF DESCRIPTION OF THE DRAWINGS

FIG. 1B shows the user/computer interface device of FIG. 1A attached to the user's forefinger.

FIGS. 1C and 1D show the interface device attached to a support stand.

FIG. 12 shows examples of display screens of operational sequences of the device.

FIG. 14 shows a block diagram of an enterprise-wide security-oriented computer system.

DETAILED DESCRIPTION OF PREFERRED EMBODIMENTS

Figure 1A:
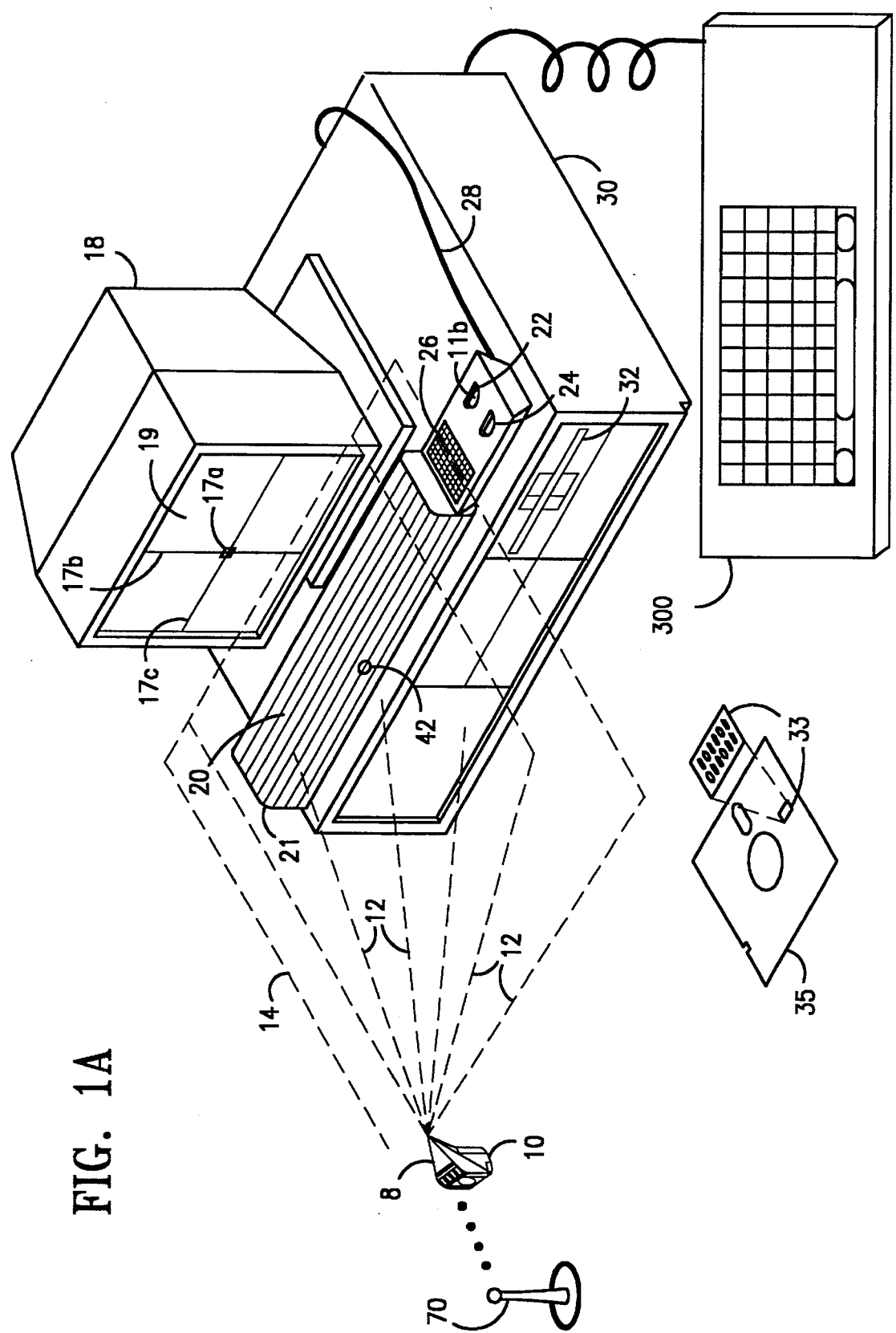
FIG. 1A illustrates a first embodiment of the present invention.

FIG. 1A, wherein like reference numerals refer to like parts, shows a first embodiment of the present invention. A wireless battery-powered user/computer interface device 10 transmits infrared user control signals 12 through signal transmission system 14, to a base/computer interface device 20, which is interconnected into a computer 30 via a cable 28.

Other electromagnetic and/or acoustic signal transmission systems can be used in the present invention. Further, a hardwired signal transmission system can also be desirable where remote wirelessness is not needed or wanted by the computer user. Hardwired versions are less costly to manufacture than wireless versions.

Signal generating circuitry (hardware and firmware) is implemented using a variety of well-known transceiver components, depending on the desired signal transmission system (e.g., infrared, radio, acoustic, hardwired, etc.).

Figure 7B:
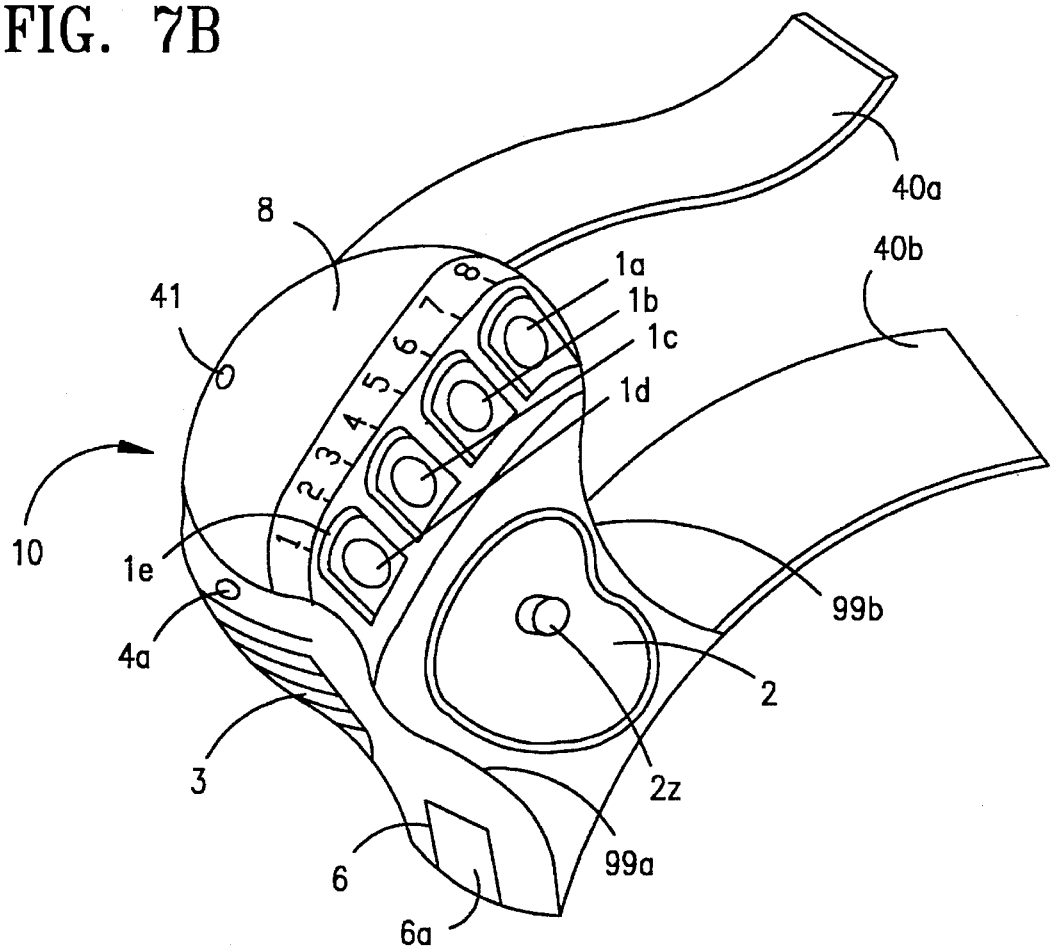
FIGS. 7A and 7B are top perspective views of first and second versions of a first embodiment of a user/ computer interface device of the present invention.
Figure 7A:
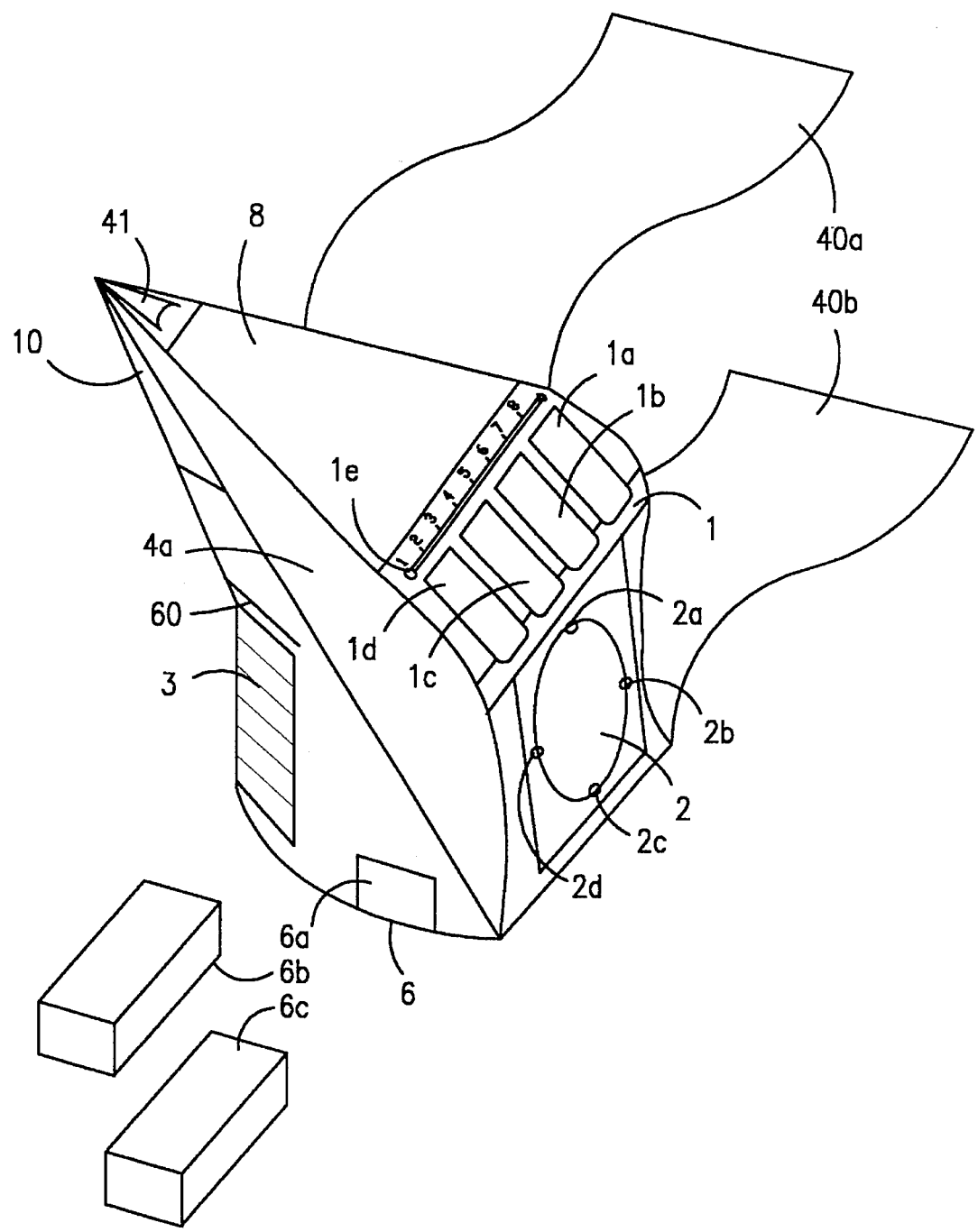

User control signals 12 are transmitted from a user/computer interface device 10 in response to a computer user's manual operation of switches mounted thereupon (see FIG. 7A for switch detail). After the user presses one or more switches on device 10 to initiate user control signals, infrared signals 12 are generated by an infrared generator comprising one or more light emitting diodes (not shown) and exit the interface device 10 through infrared lens 8. Signals 12 propagate through free space and onto base/computer interface device 20. After detection by device 20, signals 12 are demodulated, de-encrypted, converted to computer-intelligible control signals and/or other control signals, and relayed into computer 30.

Computer 30 is connected to display terminal 18. Computer 30 can also be optionally connected and/or networked with other interfaceable peripheral devices, one or more local area networks, or other centralized or distributed computers.

In FIG. 1A, display screen 19 of display terminal 18 responds to user control signals 12 and other output/display signals from computer 30, such that desired effects of signals 12 can be executed and displayed on the display screen 19.

Base/computer interface device 20 includes an optional sonic receiver element 42 adapted to receive and transmit sonic signals from device 10. Device 20 further includes lens 21 behind which stands one or more signal detectors, such as phototransistors, adapted to detect infrared user control signals 12 relayed from device 10, through wireless infrared signal transmission system 14.

The base/computer interface device 20 may also include an access key panel 26. Key panel 26 is used to enter access and authorization codes so as to limit access to device 10. Key panel 26 is a locking device, to control access to device 20, to ports 22 and 24, and to interface devices 10. Panel 26 can include conventionally known locking hardware for restricting physical access to device 20 or device 10.

Figure 8:
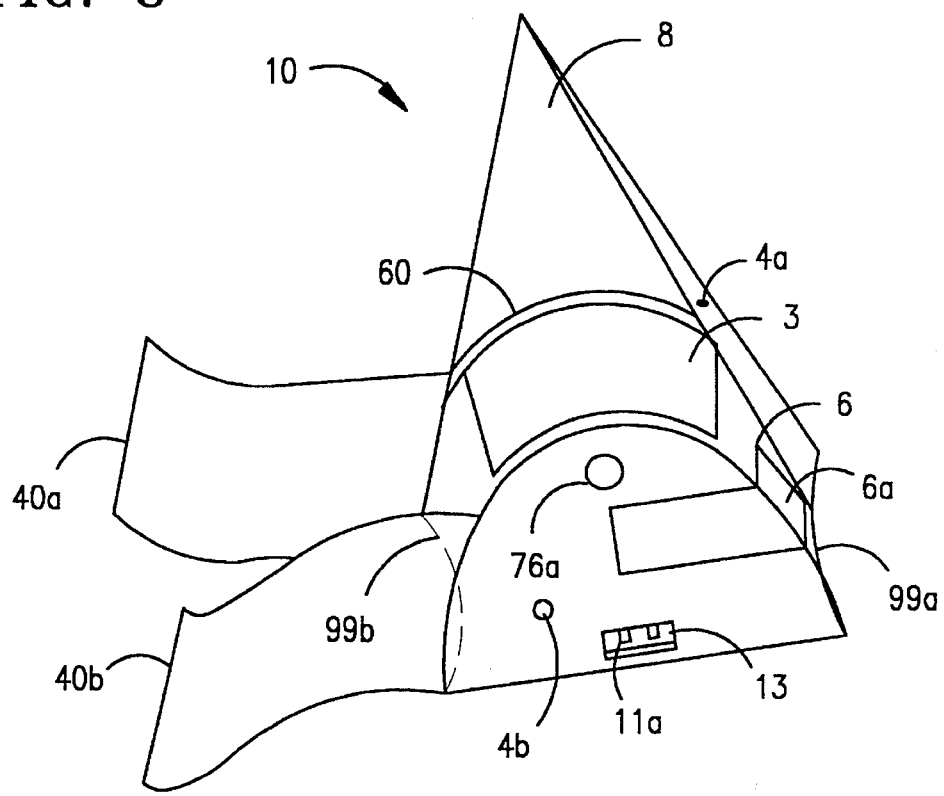
FIGS. 8 and 9 are bottom perspective views of the device of FIG. 7A.

Ports 22 and 24 on device 20 are used for recharging of batteries in the interface device 10. Device 10 includes female couplings 11a (as shown in FIG. 8), for manual coupling onto male couplings 11b to receive electrical charges for the rechargeable battery contained in device 10. Male couplings 11b are located within ports 22 and 24 in device 20. Alternatively, either a stand-alone AC/DC transformer (not shown) or the computer's serial port can also be used for recharging the interface device 10.

Display screen 19 inherently includes preprogrammed cartesian (or other conventional) positioning areas to receive cursor coordinates provided by device 10. The ordinate axis 17b and the abscissa axis 17c are shown. In addition, origin 17a is provided, through which a z-axis (not shown) is provided to assist in generation of three-dimensional displays.

Additionally, computer 30 has a floppy or other storage disk drive 32 which is adapted to receive a floppy or other suitable diskette package 35 containing digitally encoded instructions 33 for interfacing the software drivers of the present invention with the operating system software of the computer 30. A keyboard 300 is typically attached to the computer as a separate input device. However, keyboard use can be minimized or eliminated, for many important tasks, by use of the interface device 10.

Fig. 1B shows a first embodiment of device 10 attached to a computer user's forefinger.

Alternatively, as illustrated in FIG. 1C, device 10 can be attached to a support stand 70. The support stand 70 is shown in FIG. 1D. Device 10 is attached to an articulating support 72 of the support stand 70. Hooks 74a–74d as shown in FIG. 1D affix device 10 firmly onto support 72. Device 10 can be moved freely about while attached onto support 72. Support 72 plugs a concavity 76a onto ball joint 76b of support stand 70. Device 10 could also be directly accommodated onto ball joint 76b without the articulating support 72 if an appropriate concavity 76a is included. Telescopic support stand members 70a can be used to allow extension and contraction of stand 70 to different heights, to suit user preferences. Support 72 can also be used to carry other electronic components associated with device 10 operation, including additional means for creating user control signals, such as positionally activated switches.

Support stand 70 can be used in at least two basic ways: 1) with articulating support 72, or 2) without articulating support 72. When device 10 is used attached to stand 72, the feature of travelling in more than one dimension at the same time is provided by the present invention. In combination with a three-dimensional (virtual) display, the computer user can "travel" in two or three dimensions virtually simultaneously. This effect is achieved by liquid conductive switches or other position-activated switches (not shown) pointing in one virtual dimension (e.g., "x") in combination with either one or two dimensions (e.g., y" and "z") pointed to by device 10, using manually operable switches. In summary, virtual "three dimensional" travel can be achieved, which can be helpful for many applications including CAX (i.e., CAD/CAM/CAE); gaming; robotics; education; virtual microscopy; multimedia; and other so-called "virtual reality" applications.

Basic Operation

Figure 2:
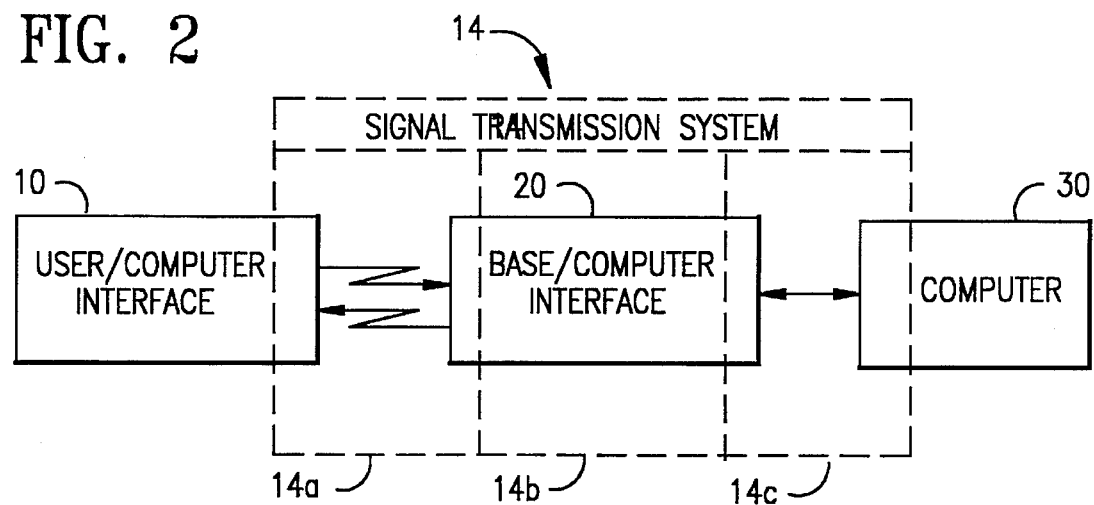
FIG. 2 is a block diagram illustrating a hardware implementation of the present invention.

Referring now to FIG. 2, an overview of the basic computer interface system is shown. Basic control elements include wireless user/computer interface device 10, signal transmission system 14, base/computer interface device 20 and controlled computer 30. Signal transmission system 14 shown includes bidirectionally operable communication channel 14a between device 10 and device 20; channel 14b within device 20, and channel 14c between device 20 and computer 30.

It is well known in the art, that many different signal transmission options are available for communicating between user devices and computers. Thus, a variety of wireless and hardwired signal transmission systems are possible with the present invention. However, infrared signal transmission is the preferred mode and is used in discussing signal transmission.

Figure 3:
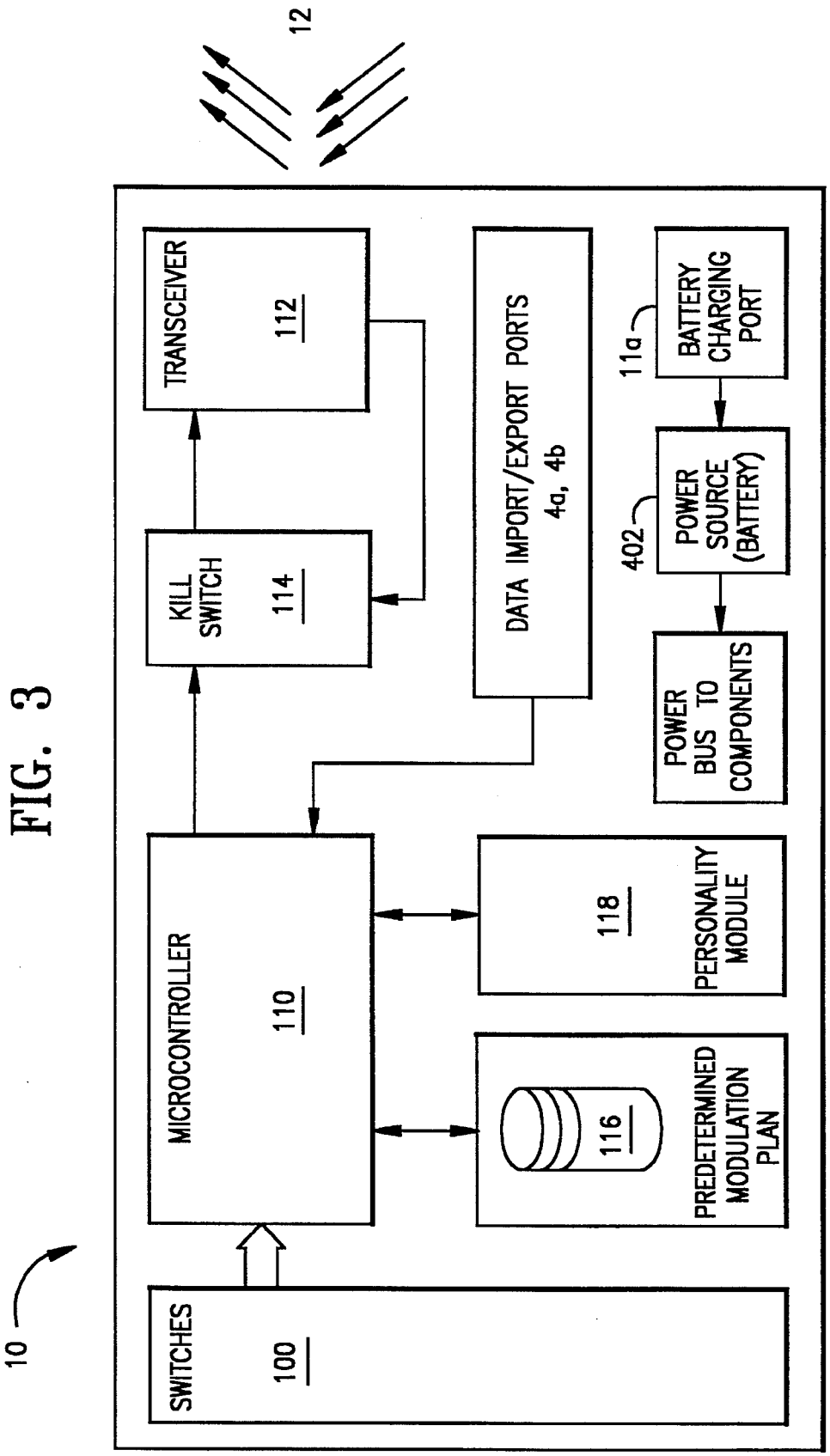
FIG. 3 is a block diagram of basic functional modules of a user/computer interface device according to the present invention.

FIG. 3 is a block diagram of the basic functional modules of user/computer interface device 10, showing the main functional modules and the functional module interconnections. Typical hardware and electronic components are arranged to perform signal-generating, signal processing, signal-terminating, and signal-transmitting functions for user/computer interface device 10.

Module 100 represents the totality of any possible number of switch arrangements implemented on any given embodiment of user/computer interface device 10. Depending on the particular embodiment, these could correspond to manually operable switches shown as switches 2, 3, 1a, 1b, 1c, 1d, and 1e of FIG. 7A or to any other feasible alternative arrangement of switching components. Alternatively, a version of module 100 can be provided which reports switch states of internal switches, based upon the position positionally activated switches.

Figure 4:
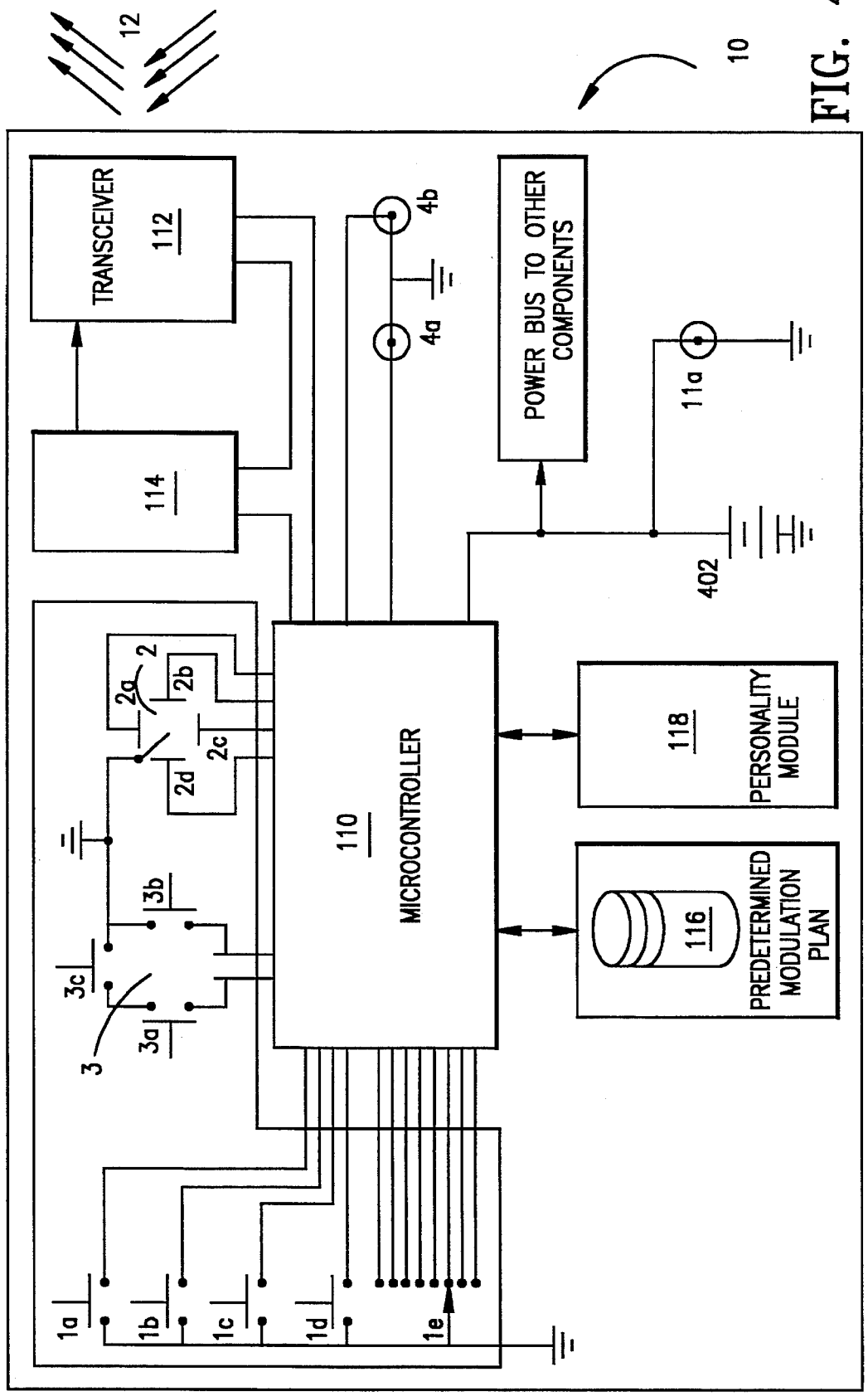
FIG. 4 is a schematic block diagram of the user/computer interface device shown in FIG. 3.

FIG. 4 illustrates switch hardware for four secondary thumbswitches 1a, 1b, 1c, 1d; for master control thumbswitch 2, for front switches 3a–3c, and for mode switch 1e. (See FIG. 7A) Switch states of switches 1a, 1b, 1c, 1d, 1e, 2, and 3 are sensed by switch position sensing module 100 and sensed switch states are communicated to microcontroller 110.

Returning to FIG. 3, module 110 represents a microprocessor or microcontroller for processing. The microcontroller 110 detects the position and/or state of the control switches comprised in module 100. Module 110 also serves to encode this information in accordance with predetermined parameters and modulation plans, using the information stored in personality ROM module 118 and ROM (or EEPROM) module 116. The result of this process is a composite signal which is then outputted from module 110 in an organized intermediate signal format and fed into module 114. In general, module 110 is implemented with the use of a microprocessor or microcontroller integrated circuit chip, whose specific functional and operational characteristics depend on the specific type of embodiment being implemented. Integrated circuits of this type are well-known in the art.

The arrows between functional modules of user/computer interface device 10, shown in FIG. 3, represent individual or grouped conductive paths to relay signal intelligence and control signals between functional modules.

Personality module 118 is a ROM memory storage device, and module 116 is a ROM (or EEPROM) device. These devices store, in protected form, information which is used by module 110 to determine the encoding scheme and other information processing parameters. In general, personality module 118 contains application-specific, environment-oriented information and codes. The information and codes are used to determine the encoding and modulation scheme to be followed by module 110, in accordance with the specific application selected by the user. Module 118 is implemented as an interchangeable ROM cartridge, that can be easily inserted and removed by the user (See FIG. 7A, modules 6a, 6b, 6c). Different ROM cartridges contain encoding and modulation plans and other information corresponding to different software applications. The user needs only to insert the ROM cartridge into device 10 which corresponds to the software application (i e., "personality operating environment") to be used.

Also, ROM (or EEPROM) module 116 is implemented in device 10 for security-oriented applications. Module 116 contains encryption security information, comprising one or more access by device 10 and authorization security tables for limiting access to any enterprise resource by: 1) one or more user(s); 2) one or more user/computer interface device(s); 3) one or more application(s); 4) one or more file(s); 5) one or more system(s); or 6) one or more network or signal transmission system communication channel(s), within the auspices of an overall, enterprise-wide access and authorization privileges plan. Access by users or devices to any given enterprise resource is either granted or denied, based upon the security clearance of the user or device or based on any other command and control information defined and customized into the access and authorization privileges plan of the specific enterprise, as administered by an authorized systems administrator. Module 116 is not designed to be installed, deinstalled, serviced, or updated by the user, but is controlled by the system or security administrator.

The actual implementation or presence of modules 116 and 118 on any given embodiment is optional and depends on the particular application and environment for which device 10 is adapted. Furthermore, the specific integrated circuit chips used to implement functions of modules 116 and 118 is also dependent on the type of application, personality operating environment, or security plan being implemented.

The output of module 110 is a composite signal which is relayed into modulator/transceiver module 112. The signal path from module 110 to module 112 passes through module 114, which acts as a kill switch. When switch 114 is open, the signal from module 110 cannot be input to module 112, and output signalling is disabled. The state of the signal path in kill switch 114 is controlled by an external signal for disabling device 10. An external kill signal is generated and transmitted by base/computer interface device 20 or other authorized signal source. A kill signal, when transmitted, is processed by transceiver module 112 of device 10, then relayed into kill switch 114. As illustrated in FIG. 4, AND gate 114a requires two logical "1" inputs, in order to continue passing the signal from 110 to module 112. A kill signal sends a logical "0" input into AND gate 114a, opening the kill switch, and thereby removing the path into module 112.

Module 112 represents a modulator/transceiver device. This device is implemented as an electromagnetic wave modulator/transmitter (for infrared or radio waves), as an electronic transducer (for sonic or ultrasonic waves), or as a signal buffer/driver (for hard wired transmission). In the case of wireless embodiments using electromagnetic wave transmission methods, module 112 uses the information conveyed to it from module 110 to modulate an electromagnetic carrier wave, either infrared or radio. The modulated signal is then radiated by means of a radiating device suitable to the frequency of the signal being radiated, or transmitted. In the case of wireless embodiments using sonic or ultrasonic waves, module 112 comprises an electronic amplifier and a sonic or ultrasonic transducer, depending on the specific means of transmission.

Module 112 produces appropriate signals 12 which propagate through free space and/or air and are received by base/computer interface device 20. The power of the radiated signal or intensity of the acoustic waves is chosen such that the signal can be picked up by device 20, while the distance between device 10 and device 20 is within the intended operating range.

Device 10 also includes data input/output ports 4a and 4b adapted to import data from, or export data to, devices interfaceable with device 10.

Figure 6:
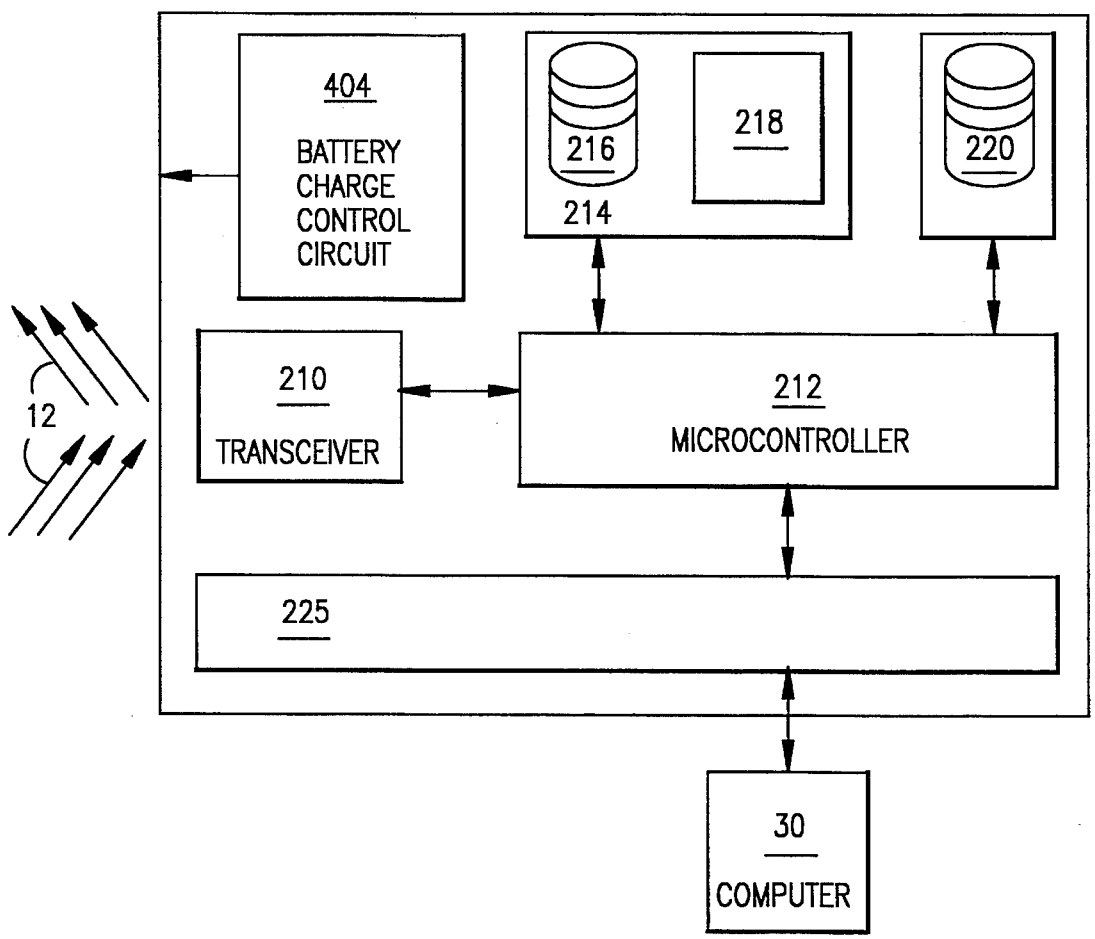
FIG. 6 is a schematic block diagram of base/computer interface device shown in FIG. 5.

Power for user/computer device 10 is provided through a battery 402, adaptable to be recharged via charge and control circuit 404 contained within base/computer device 20 (FIG. 6). Charging voltage passes through male plug 11b (FIG. 1A) which interconnects with female plug 11a of device 10, whenever device 10 is plugged into port 22.

Figure 5:
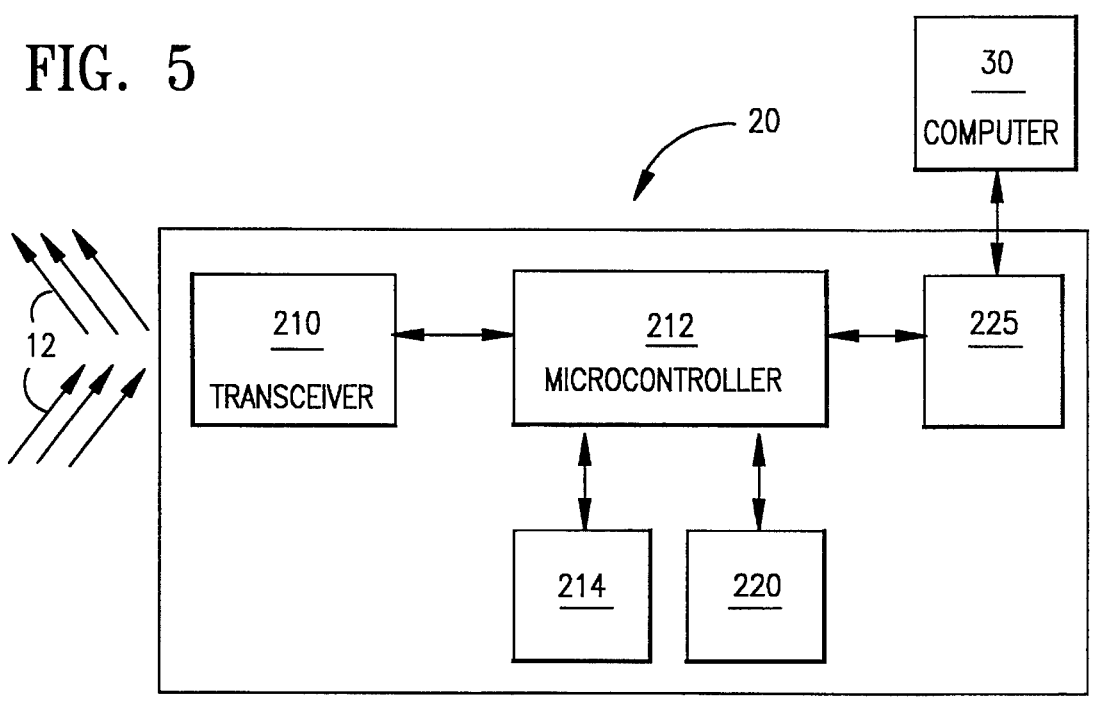
FIG. 5 is a block diagram of a computer-interconnected base/computer interface device according to the present invention.

Referring now to FIG. 5, a block diagram of the hardware arrangement of the base/computer interface device 20 is provided. Input signals 12 transmitted to device 20 are outputs from device 10. More specifically, signals 12 can comprise infrared, other electromagnetic radiation, optical and/or acoustic signals, depending on specific implementation requirements.

In FIG. 5, infrared signals 12 are received by, or transmitted out of, infrared transceiver module 210. Alternatively, or additionally, sonic and/or optical transceiver devices (not shown) can be implemented to carry sonic and/or optical signals into and out of transceiver 210. Transceiver 210 is connected to a microcontroller or microprocessor 212 to decode, or encode, signals 12. Demodulation occurs in a reverse manner to modulation, as is common practice. Information for encoding/decoding microcontroller 212 is provided by memory element 214. Memory element 214 can further comprise one or more ROM options as shown in FIG. 6. ROM 216 includes a predetermined security table and related options. ROM 218 includes a programmable security coding module option. Furthermore, a ROM or other suitable storage device 220 comprises means for modulation/demodulation of signals 12 in accordance with a preset modulation scheme implemented in user/computer interface device 10. Information in storage device 220 is used to interpret the signals 12 from device 10 according to any implemented personality environment. As a result, after incoming signals 12 are received by transceiver 210, they are supplied to the microcontroller 212 for subsequent decoding based upon information provided from memory 214 and memory 220. The decoded signals are then outputted from microcontroller 212 to a computer interface device comprised in module 225, such as a Universal, Asynchronous Receiver/Transmitter (UART) or similarly functional device.

Module 225 consists of any conventionally known computer interface device adapted to receive all original switch states generated in user/computer interface device 10, which are interpreted and stored in microcontroller 212, and to transfer those states to a computer 30. Another example of module 225 is a shift register.

Depending on the personality module implemented (such as 6a, 6b, and 6c of FIG. 7A), a plurality of different operating environments are possible. Contained within each such personality operating environment (such as security access, CAD/CAM, etc.) are a plurality of modes selected by mode switch 1e each of which, in turn, controls the functions designated by selectable switches 1a–1d.

For example, in a CAD/CAM personality operating environment, one selected mode may be "input formatting", when a user wishes to designate various input formats for the controlled computer. As a result, the secondary control switches 1a–1d designate different "input formatting" switch functions, such as coloring, shading, hatching, providing standardized geometric figures. A different setting of mode switch 1e, could involve an "output formatting" mode, with the color, style, and other "output formatting" functions being designated by the secondary control switches 1a–1d.

In general, different mode switch 1e position settings and the correspondingly different functions of switches 1a–1d (of FIG. 7A) are available for each individual personality operating environment module. This adds great operating flexibility to the present invention.

As previously noted, the cable 28 connects the output of base transceiver 20 to the input of an appropriate input port located on the reverse face of computer 30. Upon receipt of the signal outputs from base transceiver 20, the computer 30 (via driver software) then interprets the signal 242. In response, the computer 30 invokes control over the display device 18 (FIG. 1A). The computer can also invoke control over any implemented controllable peripheral device via a direct, indirect, or virtual network connection.

FIG. 7A illustrates a detailed perspective view of a first version of a first embodiment of the user/computer interface device 10. As noted earlier, device 10 includes master control thumbswitch 2, which controls positioning of the computer display cursor. Thumbswitch 2 can be very easily operated by the computer user's thumbtip, to control motion of the computer cursor in any direction (e.g., pressing locations 2a, 2b, 2c, and 2d respectively, runs the cursor up, right, down, and left) (see also FIG. 12). Coordinates 17a, 17b, 17c of FIG. 1A or other coordinates, (e.g., polar coordinates) can be manipulated. Three dimensional coordinates along a z-axis (not shown) are also available through the switch 2 when the input device 10 is configured with an appropriate three-dimensional personality module and/or mode switch 1e selects three-dimensional operation.

Device 10 also contains four adjacent, thumb-operable, secondary control switch elements, 1a, 1b, 1c, and 1d. Each of the secondary switches respectively provides a different functional choice to the computer. In other words, switches 1a, 1b, 1c, and 1d functions can be analogous to the function keys on a computer keyboard. Other switches can be mounted upon the control surface 1. The other switches can vary in number, depending upon the version of device 10, the type of computer being interfaced, the applications being used, or computer environment being served.

Mode switch 1e is a sliding switch, which slides from position 1e.1 to position 1e.8, as implemented in the user input device 10. As previously discussed, the mode switch 1e has significant operational implications in that it can be used to set the functional mode for the various functions represented by switches 1a–1d. Thus, each switch 1a–1d can, in turn, change function eight times depending upon the setting of mode switch 1e. The changing of the mode switch setting 1e thus significantly changes the operating characteristics of switches 1a–1d and, in turn, the user input device 10. When device 10 is attached to the user's forefinger, switch 1e is easily operable by the thumb.

On the front face of input device 10 is front switch 3, which can be considered a "click switch." This switch operates in an analogous fashion to selection switches typically available on "mouse-type" input devices. As illustrated, the front switch 3 can toggle upward or downward and click "on" so that data upon which the cursor rests is entered into the computer 30. The capacity to perform these and other control actions allows the user to access a variety of control options in the computer 30. In yet other embodiments, the front switch 3 can, from its' center position, "click" directly inward one or more times to perform yet other "click" or multiple "click" functions.

Still referring to FIG. 7A, a lens 8 or any other appropriately implemented signal transmissive means for transmitting predetermined selected infrared or other signal type 12 is provided. At the end of lens 8, an acoustic signal emission port 41 is illustrated. Interface device 10 can implement an acoustic emission and detection option. The acoustic port 41, in conjunction with acoustic signal generation means, can emit predetermined selected acoustic signals, when enabled. When implemented, port 41 requires a corresponding implementation of port 42 on base transceiver 20 of FIG. 1A. Port 42 is an acoustic detector, and acoustic signals emitted from port 41 are detected therewith. Any known conventional acoustic transceiver hardware can be used.

Referring still to FIG. 7A, personality module 6a is shown loaded into input device 10. The personality module 6a can be easily removed from the personality module cabinet 6. The module consists of, for example, a cartridge enclosed ROM having stored within it the various predetermined functions and data associated with the operating environment choice. Depending upon the personality module selected by the user, different primary "operating personalities" of the computer user input device 10 can be chosen by the computer user.

Alternative personality modules 6b and 6c can be selected by the computer user to implement different fundamental operating environments. Other personality modules can also be used to replace installed personality module 6a simply by removing module 6a from cabinet 6, and inserting either module 6b, or module 6c, or any other module.

Data port 4a can also be used for a variety of data inputs and outputs. When used as a data input port (e.g., to rewrite an EEPROM, for the purpose of updating security information) input port 4a affords much additional flexibility to device 10. It can be observed that 4a security updates, changing the access and authorization privileges of device 10 can help achieve objectives of the invention. When used as a data export port, data port 4a can be used to output device 10 stored data, which has been made accessible for export.

Figure 9:
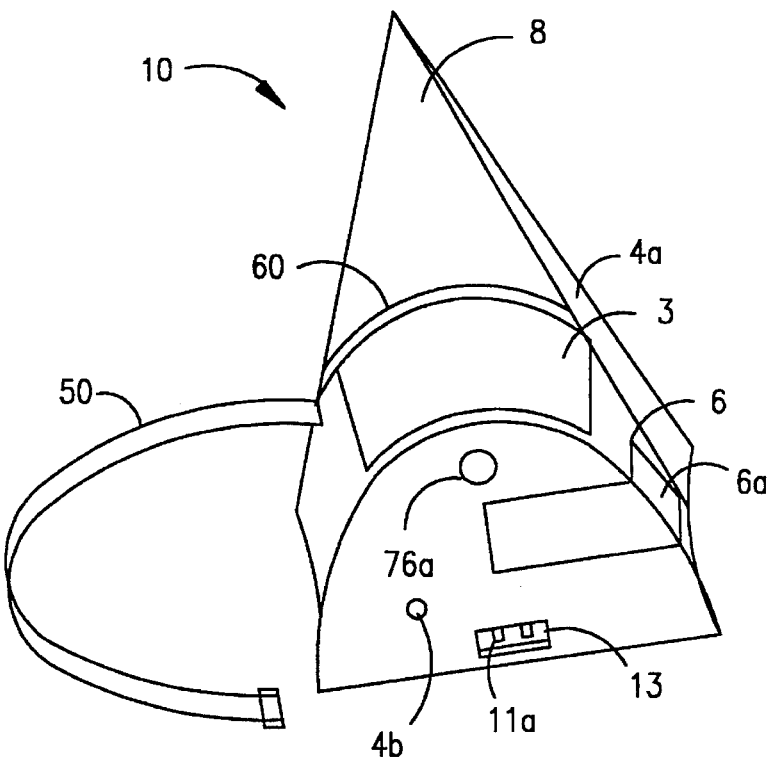

Device 10 does not require strapping to the user's hand, finger, wrist, etc., in order to operate properly. While strapping by means of a strap 40a and strap 40b is useful, strapping does not affect basic functions of device 10. Strap 40a and 40b can be padded (not shown) to provide greater user comfort. A padded lining contributes to the ergonomic design of device 10—allowing the user to comfortably wear device 10 for prolonged periods. Other strap designs or arrangements are contemplated. Other attachment means can attach device 10 to the human hand, wrist, finger, etc. For example, a ring or ring-type attachment means is shown in FIG. 9.

Prior to attaching device 10 to the left or right forefinger, straps 40a and 40b are affixed into the side of device 10 to which the user will attach his or her forefinger.

An important feature of the first preferred embodiment of device 10 is "ambidexterity." Device 10 has symmetrical, arcuate-shaped surfaces 99a and 99b which accommodate either left forefinger (99a) or right forefinger (99b) attachment with equal facility, to suit user preference or immediate needs.

Strap 40a and 40b are attached to device 10 by attachment fittings. Alternatively, "snap-in" fittings can be implemented on straps 40a and 40b, which can be snapped into complementary fitting receptacles or directly into concavities on device 10.

When straps 40a and 40b firmly encircle the forefinger phalange, affixing it into the left or right side arcuate-shaped surface 99a or 99b of device 10, strap padded lining helps to promote an "illusion of weightlessness". This "illusion" can be provided, due to the padding and substantial construction of the straps. In reality, the light weight of device 10 is made to be perceived as "featherweight" given 1) the padding, 2) the firm encirclement of the phalange, 3) the staging of device 10 when affixed to the phalange according to design, and 4) the easy balance achieved on the user's hand, given the above. FIG. 7B illustrates a second version of the first embodiment shown in FIG. 7A which contains similar elements to that of FIG. 7A except for the inclusion of thumbswitch selector switch 2z. As illustrated in FIG. 9, an alternative means for attaching the computer user input device 10 to the computer user's finger can be a releasably secured ring 50. Ring-type attachment means may be desirable for some computer user preferences. Other strap attachment means can be provided, including leather. However, it appears that Velcro(R) straps with a padded lining best achieve the "illusion of weightlessness."

Figure 10A:
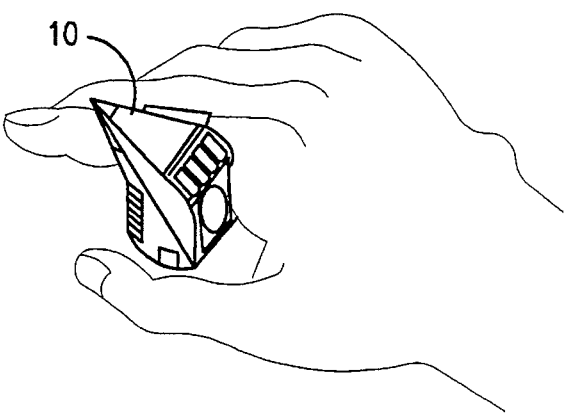
FIGS. 10A–10C illustrate devices attached to a user's left and right hand index finger.
Figure 10B:
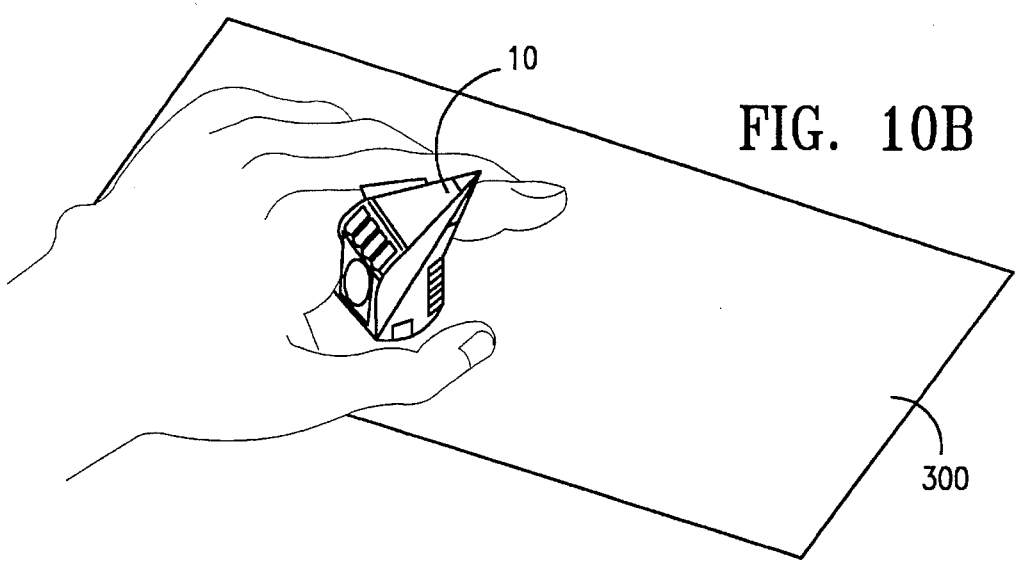
Figure 10C:
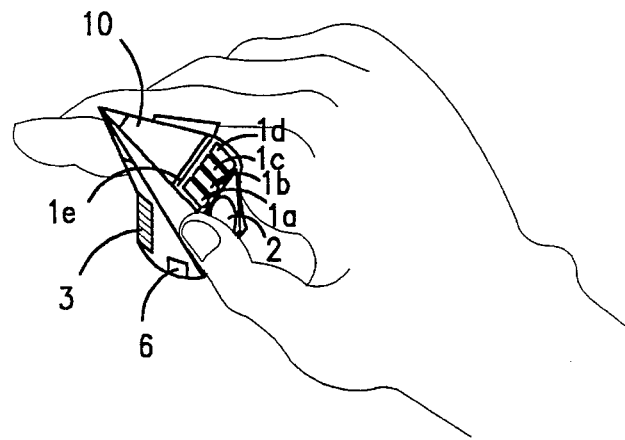

FIGS. 10A–10C show device 10 worn attached onto both of a user's forefingers. A keyboard 300 can also be used jointly with device 10 for even greater flexibility in computer control.

Figure 11A:
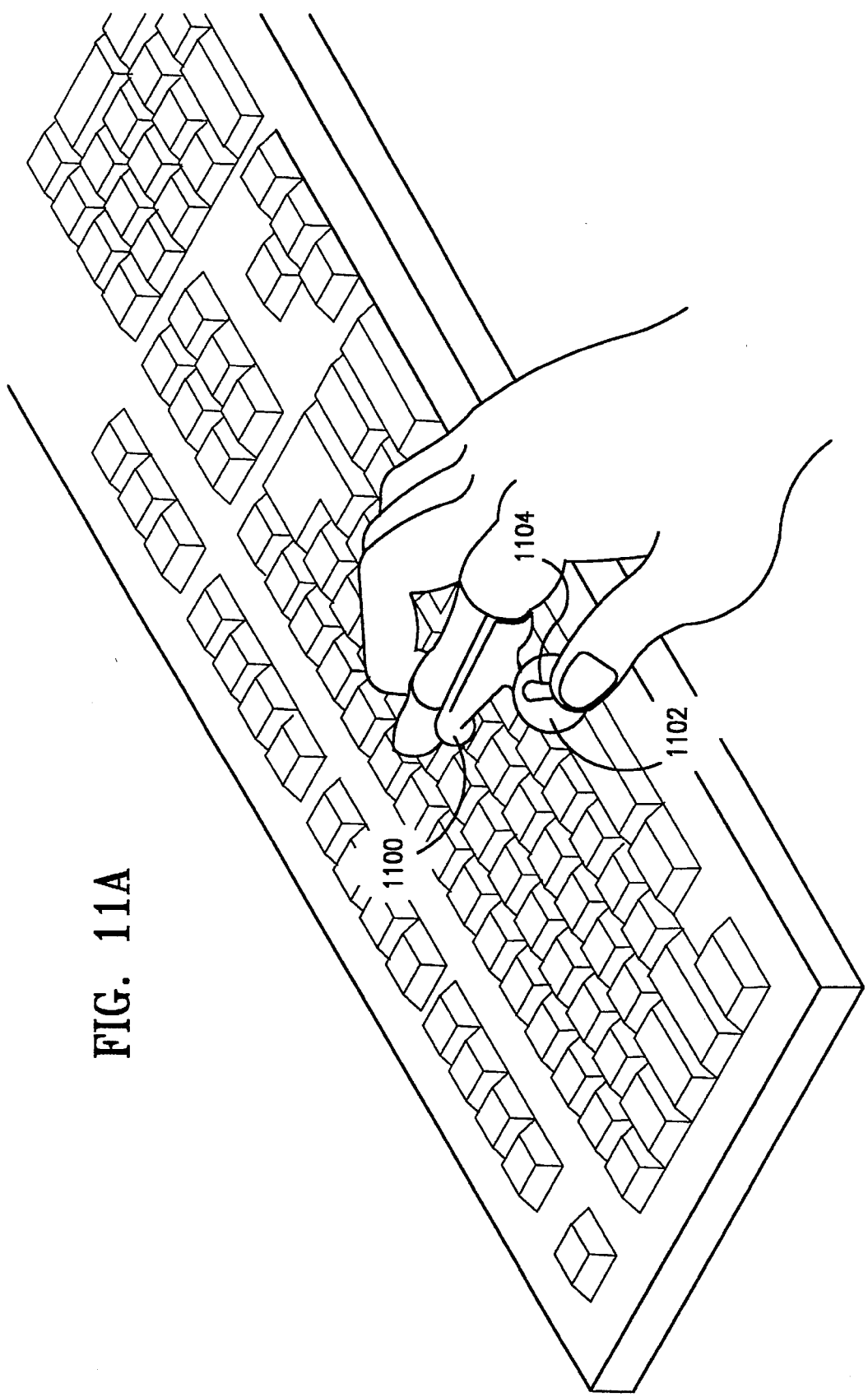
FIG. 11A is a top perspective view of a second preferred embodiment of the user/computer interface device.

Referring to FIG. 11A, a second embodiment of a user/computer interface device 1100 is shown attached onto a user's finger. The device is a simplified version of device 10 and includes only a thumbswitch 1102 and a thumbswitch selector switch 1104.

Figure 11B:
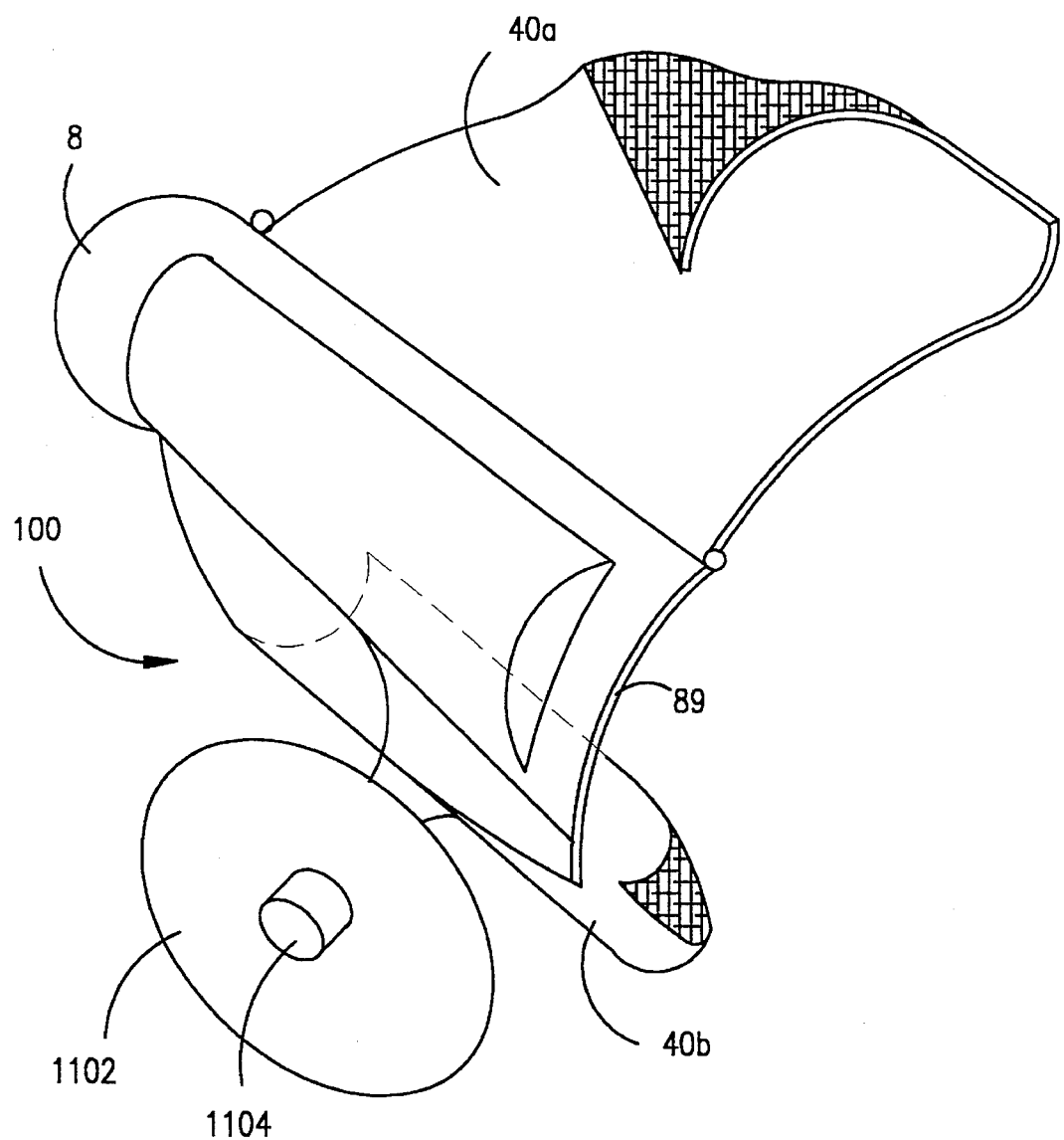
FIG. 11B is a top perspective close-up view of the device shown in FIG. 11A.

FIG. 11B is a top perspective close-up view of the second embodiment shown in FIG. 11A. The 1102 and 1104 switch arrangement operates in a similar fashion to thumbswitch 2 and front switch 3 of the first preferred embodiment, shown in FIG. 7A.

FIG. 12 illustrates control of a cursor on the display screen. Display screen 19 inherently includes a preprogrammed cartesian (or any other conventional or customized) positioning mechanism to receive cursor coordinates provided by computer 30, in accordance with user control signals 12, initiated and transmitted using device 10. As a primary point of reference, origin 1217a is provided.

FIG. 12 shows a series of different, sequential examples of cursor movement events. In screen 1204a, the default position, 1217a, is shown in the center of the screen. Screen 1204a is always the beginning screen of a cursor reinitialization and movement sequence. Default position 1217a is always presented in any basic cursor reinitialization control sequence, unless an alternative default position is customized by the user.

Computer control events, such as cursor reinitialization, movement, select functions, and "click and drag" functions, are accomplished by using one of the secondary thumbswitches 1a–1d, in combination with master thumbswitch 2 and front switch 3. As discussed above, the specific functions assigned to the thumbswitches depends upon the mode switch 1e in combination with personality module and with any application software used in computer 30.

Successive screens show a progression of directional cursor moves using user control signals initiated by thumbswitch 2. (For examples of "click and drag" action, using both thumbswitch 2 and front switch 3, see FIG. 20, which discusses usage of the present invention with "mapped keys" in a word processing application.) For example, directional pressure on switch 2 moves the cursor up in the direction of direction 2a; cursor right, 2b; cursor down, 2c; and cursor left, 2d. Other directions are implemented with appropriate switching circuitry and/or driver or other application software.

Security Control

Figure 13A:
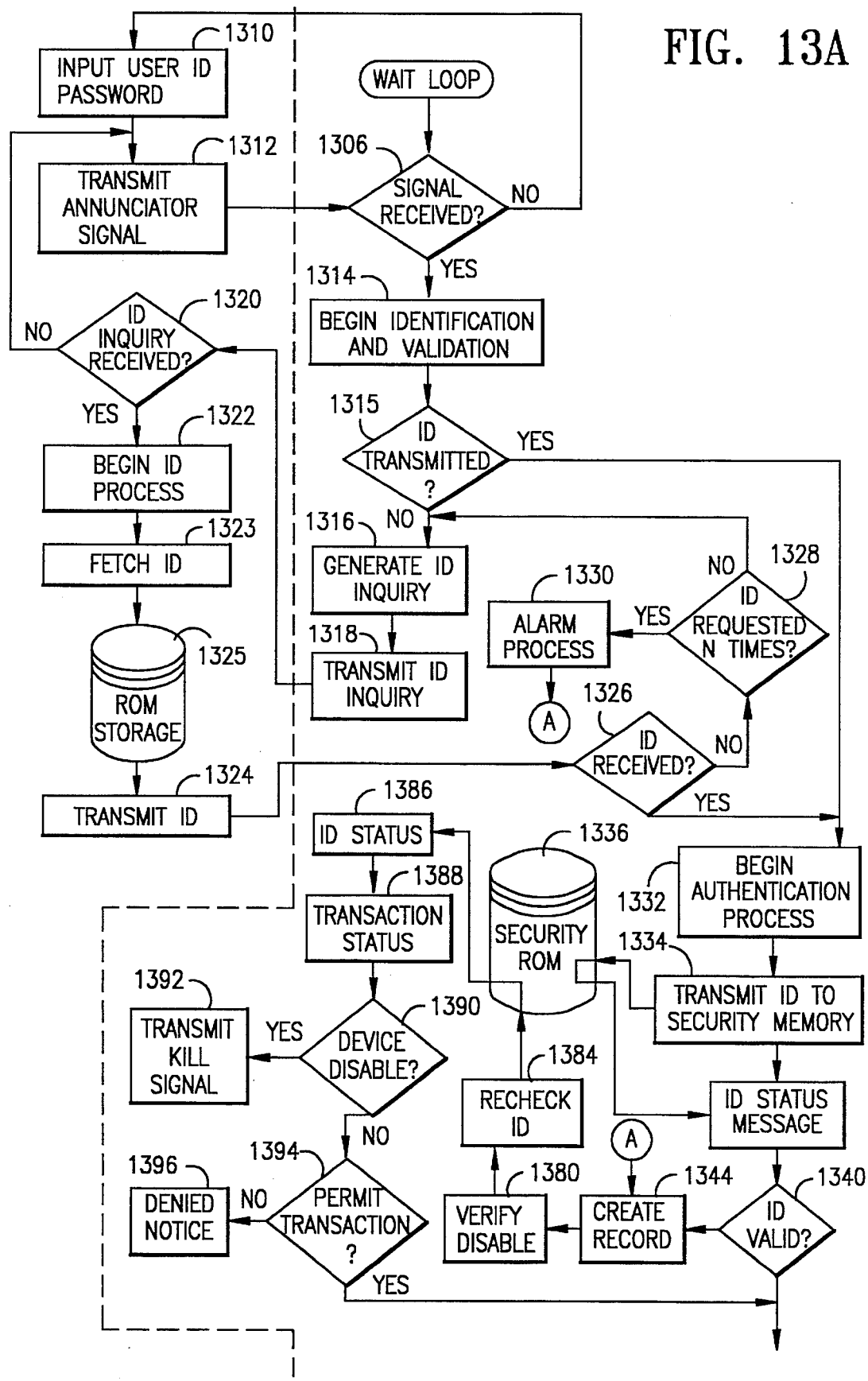
FIGS. 13A and 13B are a flowchart showing one embodiment of the security logic of a security version of the device.
Figure 13B:
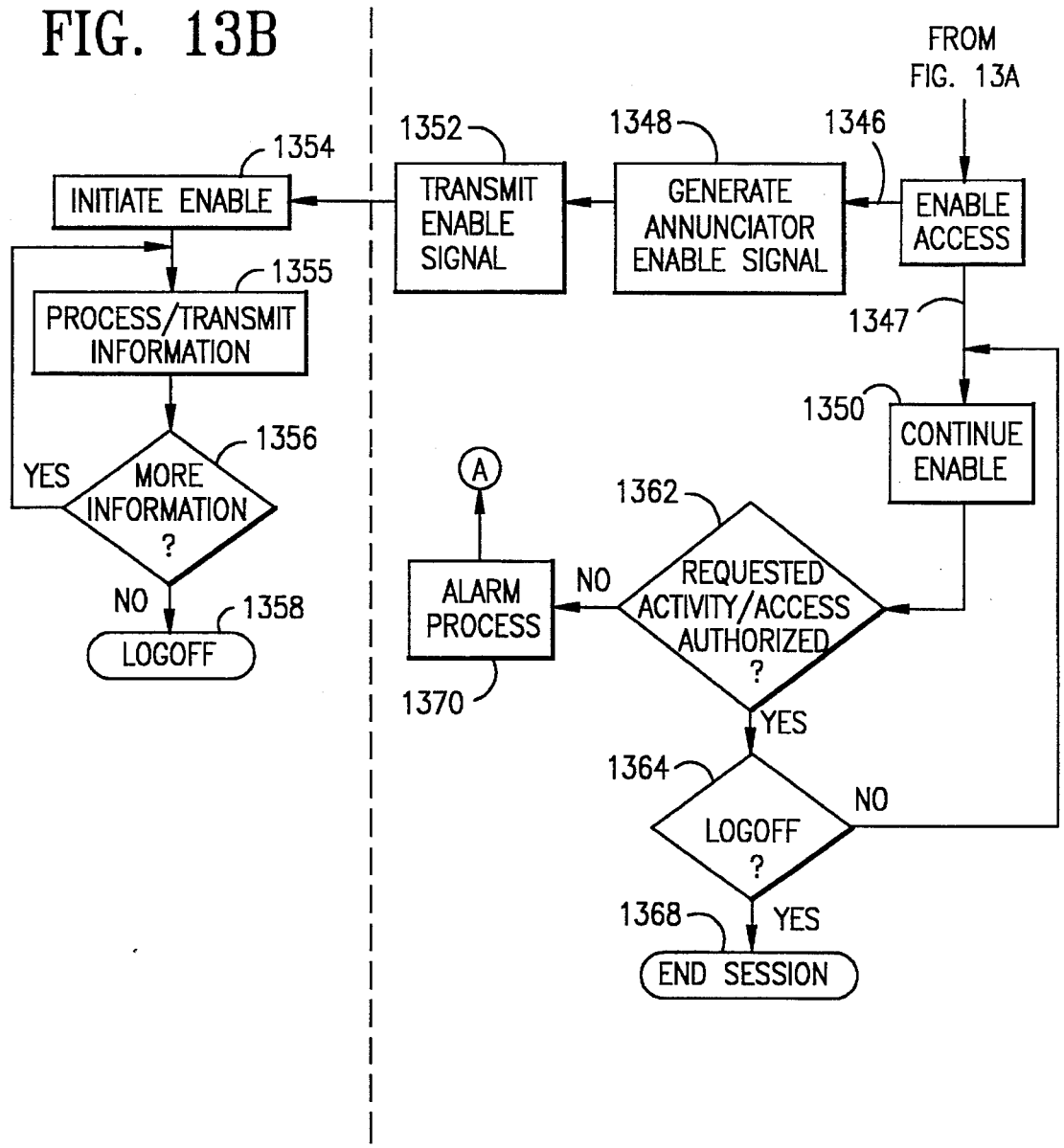

FIGS. 13A and 13B show a typical security "operating personality" environment, wherein an "annunciator" and an "interrogator" are shown in a security-oriented dialogue.

Each user/computer interface device 10 is assigned a unique "device password." In like manner, each computer user is assigned a unique password. When combined together, user passwords and device passwords form a composite password which is designated the "annunciator" password. The composite password, itself, is a unique password specifically identifying both the computer user and interface device to the security system. Each layer of one or more layers in a security system logic is designated an "interrogator." Both user and device passwords must be authorized to gain or continue computer access, i.e. to any enterprise resource, or to complete a transaction. If either password is not authorized to gain or continue access to complete the requested transaction, then the attempted transaction is determined "illegal" by the interrogator security logic. After any transaction is deemed "illegal," alarm features are activated, including activation of the kill switch 114 of device 10.

Referring now to FIG. 13A and 13B, interrogator functions are started at step 1302. The interrogator begins a wait state loop at step 1304, listening for any annunciator signal. At step 1306, the interrogator is testing for the annunciator signal receipt from any annunciator desiring access. Until the answer is "yes," the system loops, listening for input from any annunciator.

Annunciator signal generation capability is active in device 10 at step 1308, given that device 10 contains a security personality module or other means to be responsive to manual input of a computer user's password. At step 1310, the user inputs a password into device 10, and the annunciator functions are enabled.

The correct user password enables the device 10 for transmission of an annunciator signal. At step 1312, the annunciator signal is transmitted from device 10 to the cognizant interrogator. An interrogator may be located in base/computer transceiver 20 which is interconnected into the individual computer (or other access point) being accessed. Alternatively, interrogators may be located at any access points to any enterprise resource.

After an annunciator signal is received at step 1306, the process for validating and identifying the annunciator signal and identifying the user begins. At step 1315, the interrogator determines if annunciator input device 10 transmitted a composite ID along with the annunciator signal. If a complete composite ID is received by step 1315, it is authenticated, beginning at step 1332.

However, if a complete composite ID is not received at step 1315, then, at step 1316, the interrogator generates a "Who Are You" inquiry, which is transmitted at step 1318 to the annunciating device. Once the interrogator's "Who Are You" signal is received at step 1320, the annunciator processes the "Who Are You" identification request at beginning step 1322. If a complete composite ID was not sent originally, and a "Who Are You" signal is not received, then the annunciator signal is regenerated 1310 and transmitted (or retransmitted if it was missed) at step 1312.

The annunciator (device 10) authentication/ID response to the interrogator "Who Are You" inquiry begins at step 1322, after receipt of the "Who Are You" signal. At step 1323, the authentication/ID is fetched from input device 10's memory at step 1324.

Once the ID has been fetched from memory, it is transmitted at step 1325 to the interrogator, which is waiting for this complete signal at step 1326. If the signal is not received at step 1326, at step 1328 the interrogator loops back N number of times to reinitiate the authentication/identification process. Once the N number of loops have been exceeded, however, then an alarm routing is called at step 1330.

If, on the other hand, the ID signal is received at step 1326, the authentication process beings at step 1332. At step 1334, the interrogator transmits the received signal to the security memory for comparison against the authentication/ID database (module 216 of FIG. 6). At step 1336, the received authentication/ID is compared in the security database and an ID status message is then produced at step 1338. At step 1340, the authentication/ID received by the interrogator is determined to be either valid or invalid.

If the ID is valid, then at step 1346 the access enabling process is entered. Two events then occur. First, an annunciator enable signal is generated at step 1348 and the interrogator transmits the annunciator enable signal at step 1352 to the annunciator. Second, the transaction monitor routine is initiated at step 1347 to ensure that each successive attempted transaction is legal. On the annunciator side, the initial enable process is initiated at step 1354 with receipt of the interrogator-initiated annunciator enable signal. Before any enablement occurs, however, the system tests at step 1356 to determine whether more work is being done.

If the answer is yes, then the system will loop back till all work is completed and, once no more work is to be done—i.e., annunciator enablement is no longer required—the annunciator will end the session with a logoff transaction. Immediately after logoff, the device annunciator will automatically disable itself (unless other arrangement is made) and it can only be re-enabled by repeating the entire security procedure by an authorized user and device.

If the ID is invalid, a record of the ID and the attempted transaction is made in the security memory 1336 and the alarm process is initiated, step 1344.

An additional important aspect of the system is that interrogator functions can be configured by the system administrator or security administrator to be repetitive—i.e., the interrogator can be set to periodically request the annunciator/ID during the progress of any access session being made by the user/annunciator, in accordance with a policy of the computer institution or device being accessed.

In the interrogator, the "continue annunciator enable? "routine is continuously occurring in the background at step 1350. With this routine, initiated at step 1347, the security system is continuously testing to see if each specific annunciator transaction being attempted should continue to be enabled or permitted, within the context of the session. Routine 1350 can disable annunciator operation or disable any transaction at any point that the interface device annunciator steps beyond its' access and authorization privileges.

If an alarm procedure is to be activated at steps 1370, 1330 or activated by an invalid ID at step 1340, then the requested transaction and the IDs are recorded by the interrogator for security monitoring at step 1344. The interrogator then determines whether to disable the device, starting at step 1380. The ID and transaction information is again compared with the authorization and access privileges plan in the ROM 1336. If the device is to be disabled, step 1390, the kill signal is transmitted at step 1392. Otherwise, a message as to the reasons that access is being denied is presented to the user, step 1396, or the device is enabled, step 1346.

In enterprise-wide security-oriented configurations, one or more individually authorized user/annunciator(s) are granted access to enterprise resources (PCs, networks, applications, etc.) by any "interrogator" at one or more levels—i.e., the total security system logic contained in input device(s), and/or base transceiver(s), and/or LAN network server(s) and/or centralized computer(s) and/or mainframe(s)—which interrogates any annunciator seeking access, to verify that both the user/annunciator and the device/annunciator are authorized access, and what level or levels of access are authorized.

In this example, the security module contained in base transceiver 20 which interacts with input device 10 is the interrogator. Any annunciator—i.e., any input device 10—operated by any user desiring access—any authorized user/annunciator—transmits an access request signal to the interrogator.

In summary, access control begins by initiating enterprise-wide security system interrogator functions— this is typically done by the system administrator or security administrator. This occurs in similar fashion to initiating a local area network server and its' client devices (e.g., as in Novell, 3COM, or other LANs). This can also occur similar to initiating other types of centralized or distributed networks (e.g., SNA); teleprocessing systems (VTAM, TCAM, etc.); transactions processing applications (e.g., CICS) or other operating system, application, or system access method.

What is first done is to define all enterprise resources to the core security system, and access/authority levels of these system resources, as is already known in the art of computer security. Then, all user/annunciators are defined to the security system to provide a complete deterministic, closed system, accessible only to authorized devices and users in accordance with individually assigned access privileges under a defined access and authorization privileges plan.

The present invention adds the unique features of 1) an access-seeking user/annunciator which must access user/computer interface device 10 with a password; and 2) after a satisfactory user access, device 10 then transmits its' own composite annunciation signal; and 3) distributed or centralized security logic then authenticates that specific input device 10's annunciation signal and allows only access authorized to that specific device 10 and that specific user.

Referring now to FIG. 14, groups of computers are shown arrayed within a computing institution or enterprise.

One or more properly authorized users (using one or more properly authorized devices 101–110 of the type of device 10 of FIG. 1A) in the local area network (LAN) shown in FIG. 14 can gain access to any computer on the LAN implementing the present invention, under the organizational auspices of an all-encompassing, enterprise-wide, security-oriented access and authorization privileges plan. Such a plan is shown below in Table A In summary, the 120 computer, 6 LAN enterprise of FIG. 15, has defined in its' access and authorization privileges plan, such that only four grandmaster (I, II, III, and IV) input devices need to be authorized access to all 120 computers. While each LANs' group of ten input devices could be implemented to access one or more other LANs' computers, in this example, only "grandmasters" access all six LAN groups' computers.

Access and authorization privileges plans can vary from simple network definitions, to advanced, meshed, layered network definitions. Advanced access and authorization plans can include definitions which control access to complex networks with inter-LAN gateways, access to other centralized or distributed computers such as mainframes, or any other enterprise resource definitions suitable to the enterprise's needs.

TABLE A

| CUID # | AUTH. COMPUTER(S) | AUTH. LEVEL(S) | USER NAME |
|---|---|---|---|
| 101 | ALL | ALL (I–V) | SYSTEM ADMIN/GRAND MASTER |
| 102 | "2, 3, 4, 5, 6" | I, II | DATA ENTRY |
| 103 | "2, 3, 4, 5, 6" | I, II | DATA ENTRY |
| 104 | "2, 3, 4, 5, 6" | I, II, III | DATA ENTRY SUPERVISOR |
| 105 | "9, 10, 11" | ALL | ENGINEERING |
| 106 | "9, 10, 11" | ALL | ENGINEERING |
| 107 | "9, 10, 11, 12, 13" | ALL | ENGINEERING SUPERVISOR |
| 108 | ALL | I, II | DATA COMMUNICATIONS |
| 109 | "13, 14, 15, 16" | I, II, III | PERSONNEL |
| 110 | "17, 18, 19, 20" | I, II, III | ADMINISTRATION |

Two reasons for implementing such a method and apparatus approach, are 1) the need for one or more levels of security; and 2) the need for controlled "user and device portability" to allow access by any authorized user to any authorized enterprise resource. The access and authorization privileges aspects of the present invention are highly flexible, and can be implemented in a number of ways, to suit virtually all user needs. A system administrator only needs to define users, define devices, define one or more levels of access, and define enterprise resources in order to develop an access and authorization privileges plan.

Figure 15:
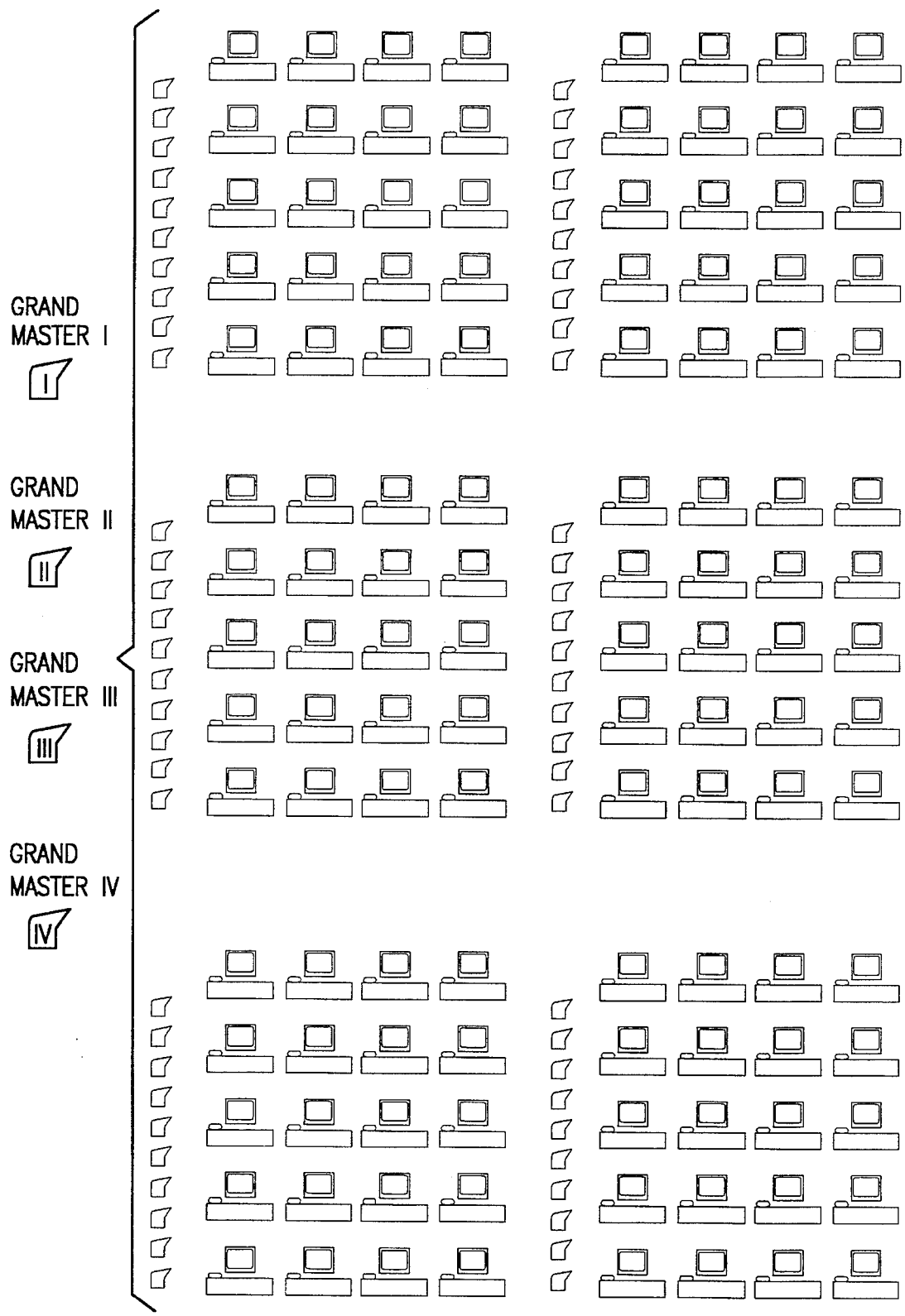
FIG. 15 shows a block diagram of an extended, meshed, enterprise-wide security-oriented network.

An extended enterprise-wide computer control system is shown in FIG. 15. Six LANs comprised of twenty computers each are shown. All twenty computers "local" to each LAN are controlled by ten "local" user input devices associated with each respective LAN. FIG. 15 thus illustrates an implementation of the present invention which has subdivided an enterprise-wide group of one hundred twenty computers into six LAN operating groups which each operate as separate LANs. Separately, shown to the left of the 120 computers, are four "grand master" input devices, labelled I, II, III, and IV. Each of these grand master input devices can access all 120 of the enterprise's computers. By virtue of their "grand master" status, each can operate on all six LANs shown.

Packet Byte Maps

Figure 16A:
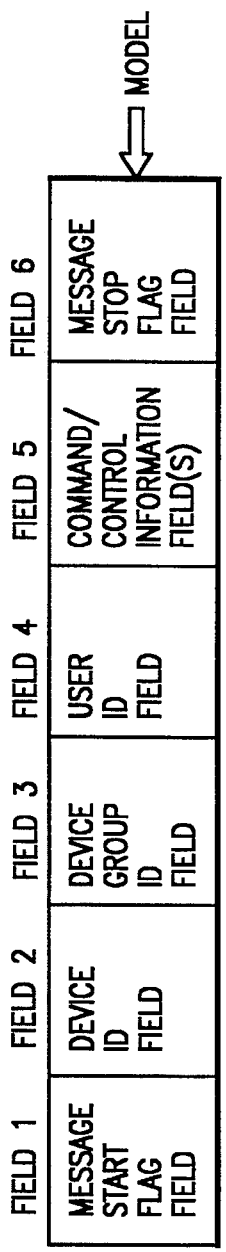
FIGS. 16A, 16B, 16C.1–16C.4, and 16D show general byte maps of user control signals in the form of message packets.
Figure 16B:
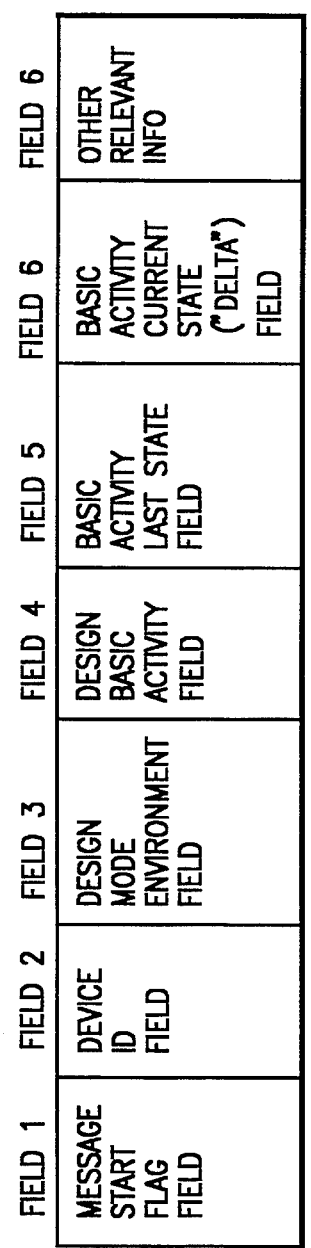

FIGS. 16A, 16B, and 16C.1–16C.4 each show a table illustrating examples from different classes of user control signals. These signals are represented in message packets. Device 10, using the personality modules, can transmit a plurality of distinct user control signals based upon different encoding sequences. Control signals are transmitted as bursts of coded pulses comprising one or more message packets. Each message packet includes a plurality of fields of encoded characters. The type of control signal determines the packet fields and organization. The format of the message packet is determined by the selected personality module.

FIG. 16A illustrates the message packet format for computer control, which includes a high-level, security-oriented ROM personality module 118 (FIG. 3) or for use of the security EEPROM 116 (FIG. 3). Field 1 is a flag indicating the start of the message packet. Fields 2–4 provide ID information designating the device and the user. This information is used to determine proper authorization privileges in the annunciator/interrogator dialog. (See FIG. 13) The command/control information is contained in field 5. This information relates to the setting of the switches on device 10 and provides the actual computer control signals. These fields are shown Below in Table B

TABLE B

FIELD:

1 WAKE-UP DETECTION CIRCUITRY / MESSAGE FOLLOWS /
2 UNIQUE DEMCE ID & TIME-STAMP & PRIVILEGES

TABLE B-continued

FIELD:

3 UNIQUE DEVICE GROUP ID & TIME-STAMP & PRIVILEGES
4 UNIQUE USER ID & TIME-STAMP & PRIVILEGES
5 USER COMMAND/CONTROL SIGNAL 2D.1 CONTROL/SIGNAL MESSAGE PACKETS     2D     1.01, 1.02, ...

Finally, a stop flag indicates the end of the packet. Security functions can be included with other processing information. If security is implemented, the ID information fields are included at the beginning of each message packet. The remaining function information is contained in the succeeding fields.

FIG. 16B illustrates a message packet for a CAX personality module. Fields 1 and 2 start the message and relate ID information similar to the security-oriented packet of FIG. 16A. In addition, information defining the personality environment can be included in the beginning fields. Field 3 contains design mode information, such as a manufacturing or electrical design mode. For example, the design mode can be determined by the setting of mode switch 1e. Fields 4–6 contain the basic command function data, such as "insert" "delete" and "create a point." These fields are shown below in Table C

TABLE C

FIELD:

1 WAKE-UP DETECTION CIRCUITRY / MESSAGE FOLLOWS /
2 USER'S UNIQUE ID
3 DESIGN MODE
        MANUFACTURING DESIGN
        ELECTRICAL ENGINEERING DESIGN
        ARCHITECTURAL DESIGN
        MUSICAL NOTATION
        ETC.
4 BASIC ACTIVITY
        INSERT
        DELETE

The command function data or user control signals would generally be designated by pressing switches 1a–1d. Some functions are defined in relation to the previous function performed. Therefore, fields 5 and 6 are used to provide the prior function state and change. Any additional information or control data required for a specific function is included in field 7. An end message flag would also be included for this packet.

FIGS. 16C.1–16C.4 illustrates other user control signals. FIG. 16C.1 and Tables D, E, F and G below

TABLE D

| | | |
|---|---|---|
| 1.01 ANNUNCIATE | 1.05 CONNECT | 1.09 |
| 1.02 AUTHORIZATION | 1.06 BOOT (WARM) | 1.10 |
| 1.03 ENERGIZE | 1.07 INSERT | 1.11 |
| 1.04 DE-ENERGIZE | 1.08 DELETE | 1.12 . . . |

TABLE E

| | | | | |
|---|---|---|---|---|
| 2.01 UP | 2.05 | RESERVED | 2.09 | CLICK |
| 2.02 RIGHT | 2.06 | RESERVED | 2.10 | DOUBLE CLICK |
| 2.03 DOWN | 2.07 | RESERVED | 2.11 | TRIPLE CLICK |
| 2.04 LEFT | 2.08 . . . | RESERVED | | |

TABLE F

| | | | | | |
|---|---|---|---|---|---|
| 3.01 | CLICK | | 3.04 | DRAG | 3.07 |
| 3.02 | DOUBLE CLICK | | 3.05 | CUT & PASTE | 3.08 . . . |
| 3.03 | TRIPLE CLICK | | 3.06 | MOVE | |

TABLE G 4.01 EXECUTE 1a FOR SELECTED MODE SWITCH SETTING
4.02 EXECUTE 1b FOR SELECTED MODE SWITCH SETTING shows functions used to initiate processing on a system. After successfully accessing a specific computer or other resource, cursor movement and an example format for cursor control are illustrated in FIG. 16C.2 and Table H below.

| FIELD: |
| --- |
| WAKE UP DETECTION CIRCUITRY/SIGNAL FOLLOWS |
| 1: INTERROGATOR ID FIELD (SIGNAL-ORIGINATING INTERROGATOR) |
| 2: TARGET DEVICE ID FIELD (DEVICE ID BEING "KILLED") |
| 3: EXCEPTION CODE FIELD (REASON WHY KILL SIGNAL WAS TRIGGERED) |
| 4: ALARM PRIORITY CODE (IF APPLICABLE) |
| 5: KILL SIGNAL AUTHORIZATION SER. NO. ASSIGNED BY HIGHEST AUTHORITY INTERROGATOR (WHEN MULTIPLE LAYERS OF SECURITY APPLY) OR BY KILL SIGNAL ORIGINATING INTERROGATOR WHEN ONLY ONE LAYER OF SECURITY APPLIED |
| 6: KILL SIGNAL, WITH TIME STAMP |
| 7: STOP FLAG, INCLUDING "WRU", TO ENSURE KILL SIGNAL WAS RECEIVED (IF DEVICE BEING KILLED RESPONDS, THIS TRIGGERS SENDING OF ANOTHER KILL SIGNAL, UNTIL "NO RESPONSE") |

For function processing, the mode, i.e. the setting for switch 1e, is needed, and is included in field 5. When function keys 1a–1d are pressed, the indicated key meaning is included in field 7 (FIGS. 16C.3 and 16C.4) and Tables F and G below. The meaning is also affected by the mode referenced in field 5.

For each message packet, the base/computer interface device 20 determines the type of packet and the relevant information contained in the packet. Appropriate control signals are generated and transmitted to the computer 30 to execute the functions.

Figure 16D:
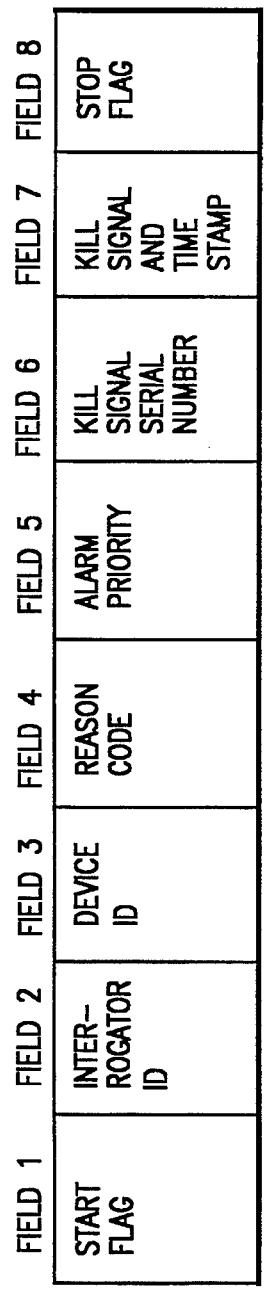

FIG. 16D and Table H below illustrates a message packet for a control signal from the base/computer device 20 to the user/computer interface device 10. The bidirectionality of the signal transmission system allows for signals both to and from the base/computer interface device 20. The packet fields are used to transfer information for activating the kill switch due to improper access requests.

Figure 17:
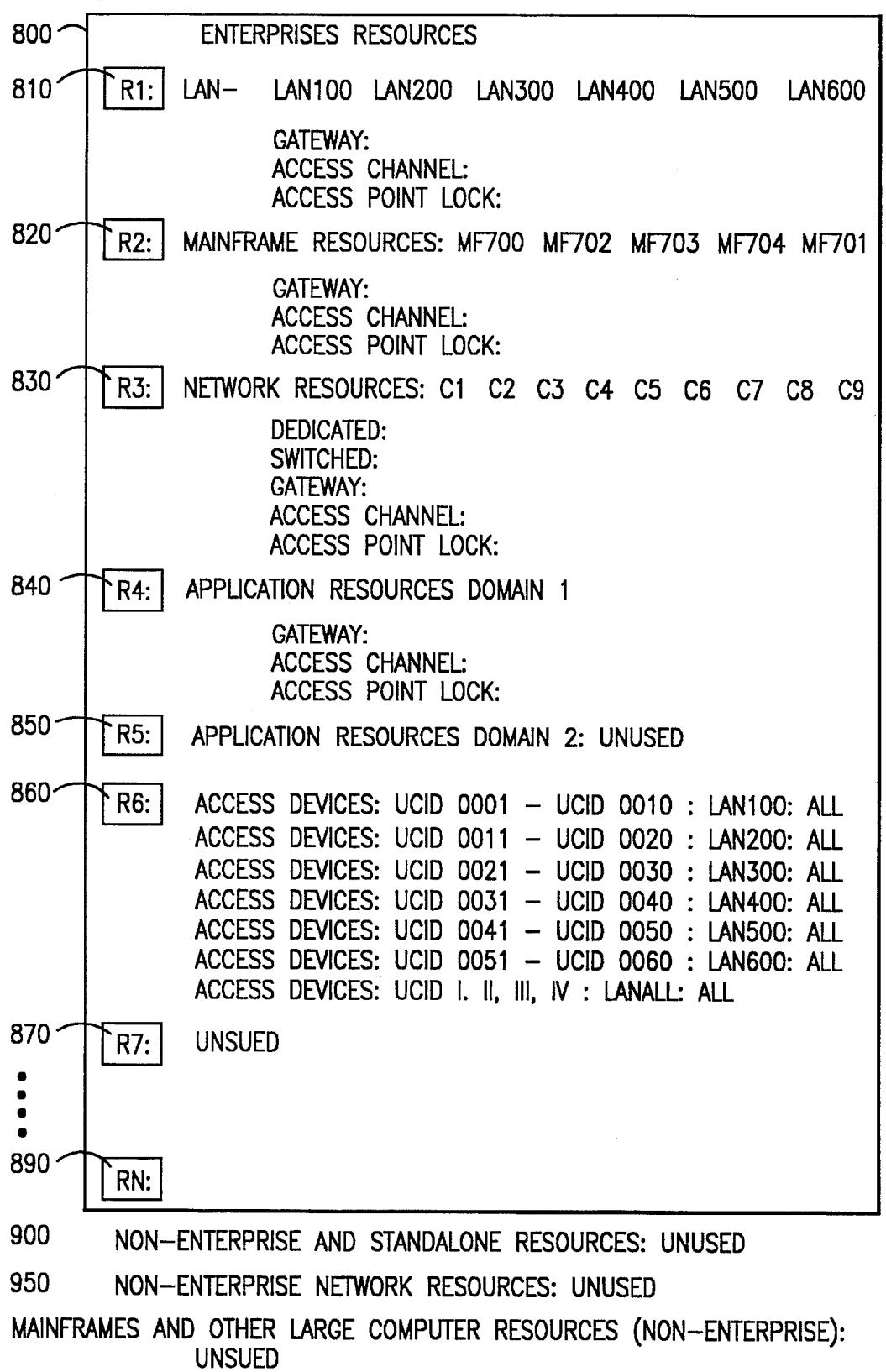
FIG. 17 shows an example of access and authorization privileges in a large, enterprise-wide implementation.

FIG. 17 shows a table, indicating an example of the general organization of a predetermined access and authorization privileges plan, developed for the purpose of safeguarding access to confidential data and restricting access to enterprise resources, as needed to satisfy a wide range of user requirements.

FIG. 17 shows an example of one possible enterprise-wide access and authorization privileges plan. Enterprise resources 800 comprise resource categories R1 through RN.

R1 resources 810 comprise six separate LANs—LAN100 through LAN600, as illustrated in FIG. 15. R2 resources 820 comprise mainframe resources accessible in enterprise-wide network 800. R3 resources 830 comprise network resources, including communications channels used within enterprise resources 800. R4 resources 840 comprise application resources which can include teleprocessing monitors, database applications, spreadsheet applications, network applications, etc. R5 resources 850 are not used, in this example, but can be made available at a future time. R6 resources 860 comprise the set of all user/computer interface devices 0001 through 0060 and grandmaster devices I, II, III and IV.

Separately, each authorized computer user, using enterprise resources 800, is assigned an unique password identification. In combination with the password of any interface device 0001—0060, shown as R6 resources 860—a user password will allow the user to access any enterprise resource for which he/she is authorized access, to the extent that the user/device composite is allowed.

To summarize, users are assigned passwords for the purpose of accessing at least one user/computer interface device; and, after accessing device 10, for accessing one or more specific computers, applications, or any other enterprise resource, to which the user is authorized access. With this method, computer users do not access the computer directly. Users access user/computer interface devices, which in turn access computers using a combination user password and a device password.

An access and authorization plan can be implemented in the operating system software; applications software; ROMs; and/or EEPROMs, depending on user needs and implementing means chosen.

In one implementation, the access and authorization information is stored in the electrically-erasable programmable read-only memory ("EEPROM") 116 (FIG. 3) of device 10. The information can include unique identifying data for the device or user for use in security-oriented applications. To reflect changes in the organization, an EEPROM programmer device, in conjunction with specialized data input ports 4a and/or 4b, can be used to repeatedly change or update EEPROMs.

Figure 18A:
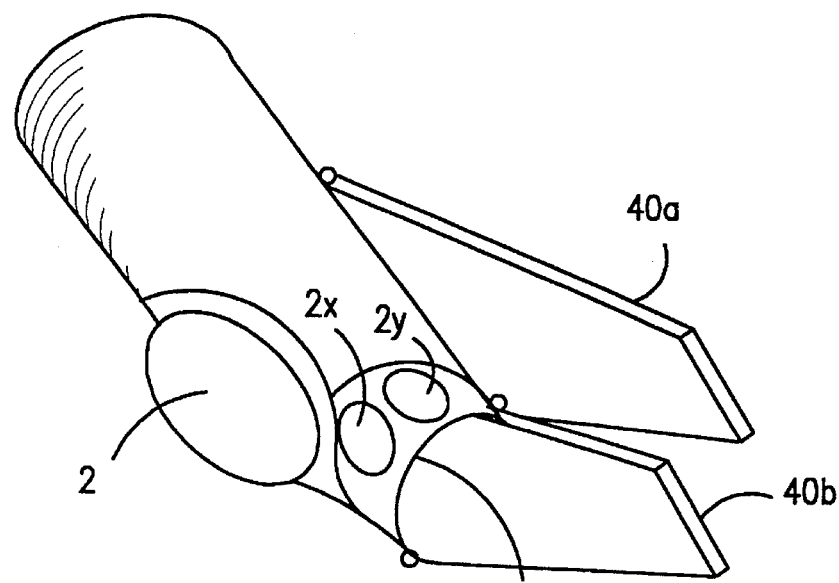
FIGS. 18A and 18B show top perspective close-up views of a third embodiment of the user/computer interface device.
Figure 18B:
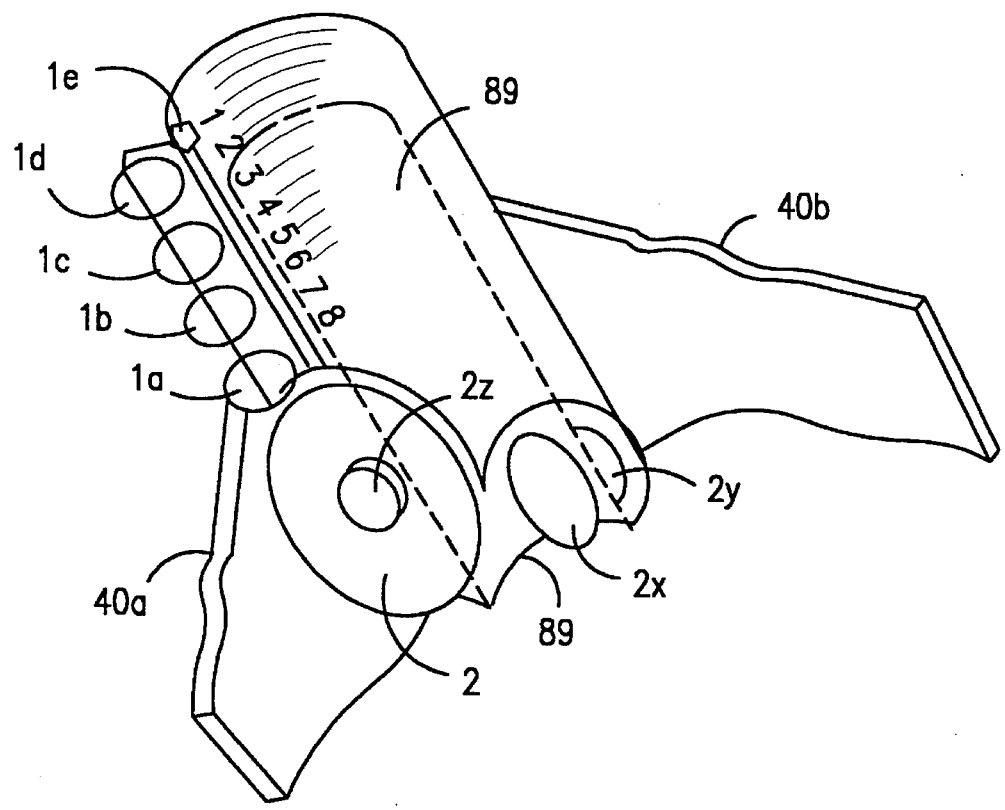

FIG. 18A shows a basic version of a third embodiment of device 10. FIG. 18B shows an advanced version. Both versions can be attached to the left or right forefinger.

The third embodiment, comprising several versions, is especially adapted for computer input and control needs of users with mobility impairments or other serious physical handicaps. The embodiment shown in FIGS. 18A and 18B are specifically adapted for attachment to the user's right forefinger. Devices of the third embodiment are explicitly designed to serve the market niche often referred to as the "assistive technologies."

Much of the discussion applicable to the first embodiment applies to the third embodiment, in terms of means to enable it. One arcuate-shaped surface 89 is available to accommodate the left or right forefinger. This is in contrast to the two arcuate-shaped surfaces 99a and 99b of the first embodiment (FIG. 7A).

Straps 40a and 40b operate to encircle the proximal phalange of the forefinger and affix it into arcuate-shaped surface 89. Also, the third embodiment shows a different placement of personality module cabinet 6, in FIG. 18B. As in the first preferred embodiment, interchangeable ROM cartridges (such as 6a, 6b, and 6c of FIG. 7) are used therein.

Figure 19A:
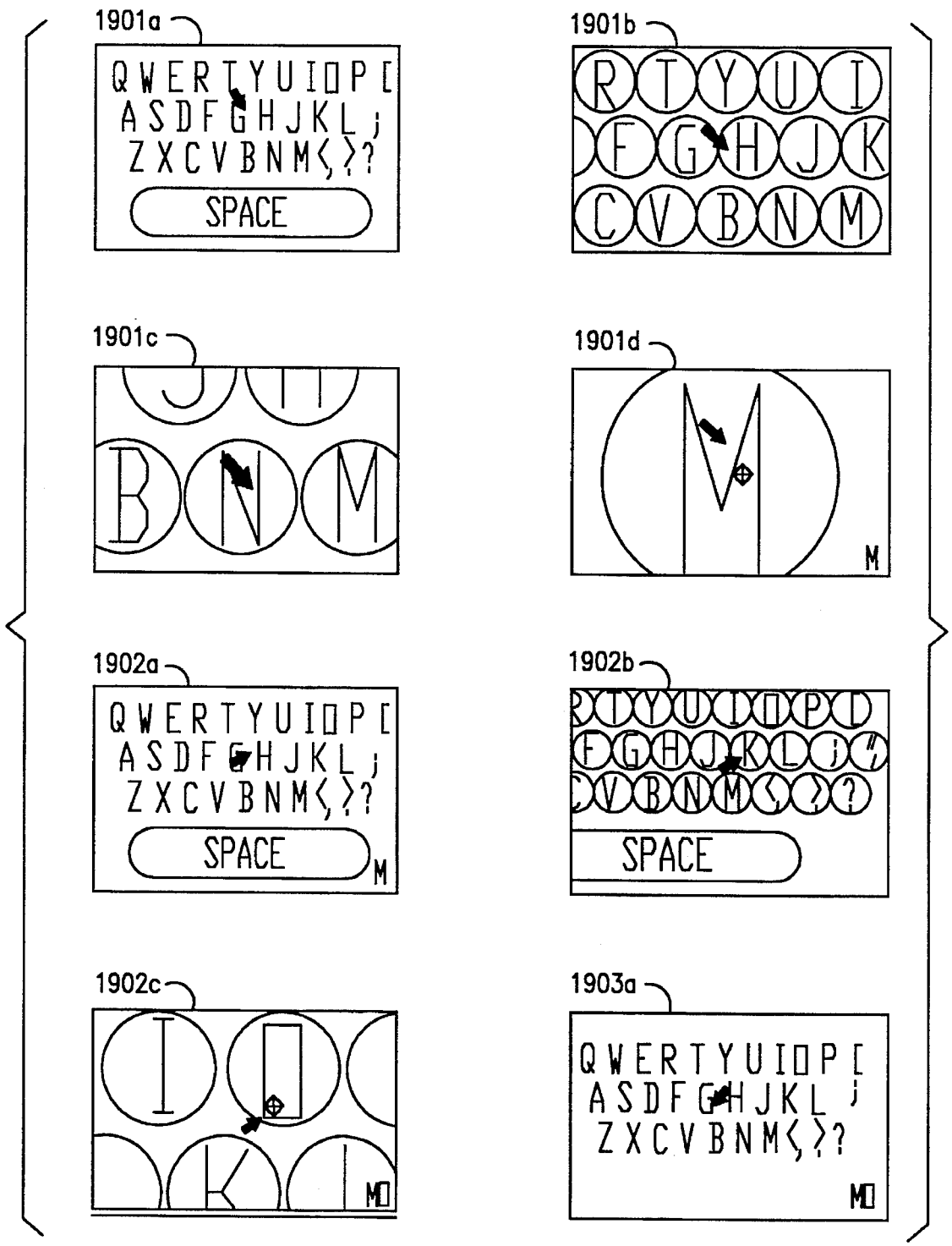
FIGS. 19A and 19B show examples of the interface device operation.

FIG. 19A shows a "mapped keys" application for use in word processing in connection with the interface device of the present invention. Device 10 can be used to move the cursor over one or more "expanding maps" of keyboard layouts. The user can then select "mapped keys" to spell out words without need of a keyboard. In this application, the user is presented with successive expanding screens of letters and numbers in the format of the keyboard layout of the user's choice. An area of the displayed keyboard is selected according to the direction of cursor movement. Upon arriving at the chosen character, the user selects it. This seek-and-select procedure is repeated, to select a series of characters in succession until the desired word is spelled out.

The screens can display a standard QWERTY keyboard layout or any customized key layout can be used, to suit user preferences.

In FIG. 19A, successive screens 1901a, 1901b, and 1901c show expanding screens "zooming-in" on an area of a displayed keyboard layout, according to the direction of cursor movement. Upon arriving at the chosen character, the user selects it, as in screen 1901d, which shows selection of the letter "M". Screens 1902a, 1902b, and 1902c show selection of the letter "O".

Figure 19B:
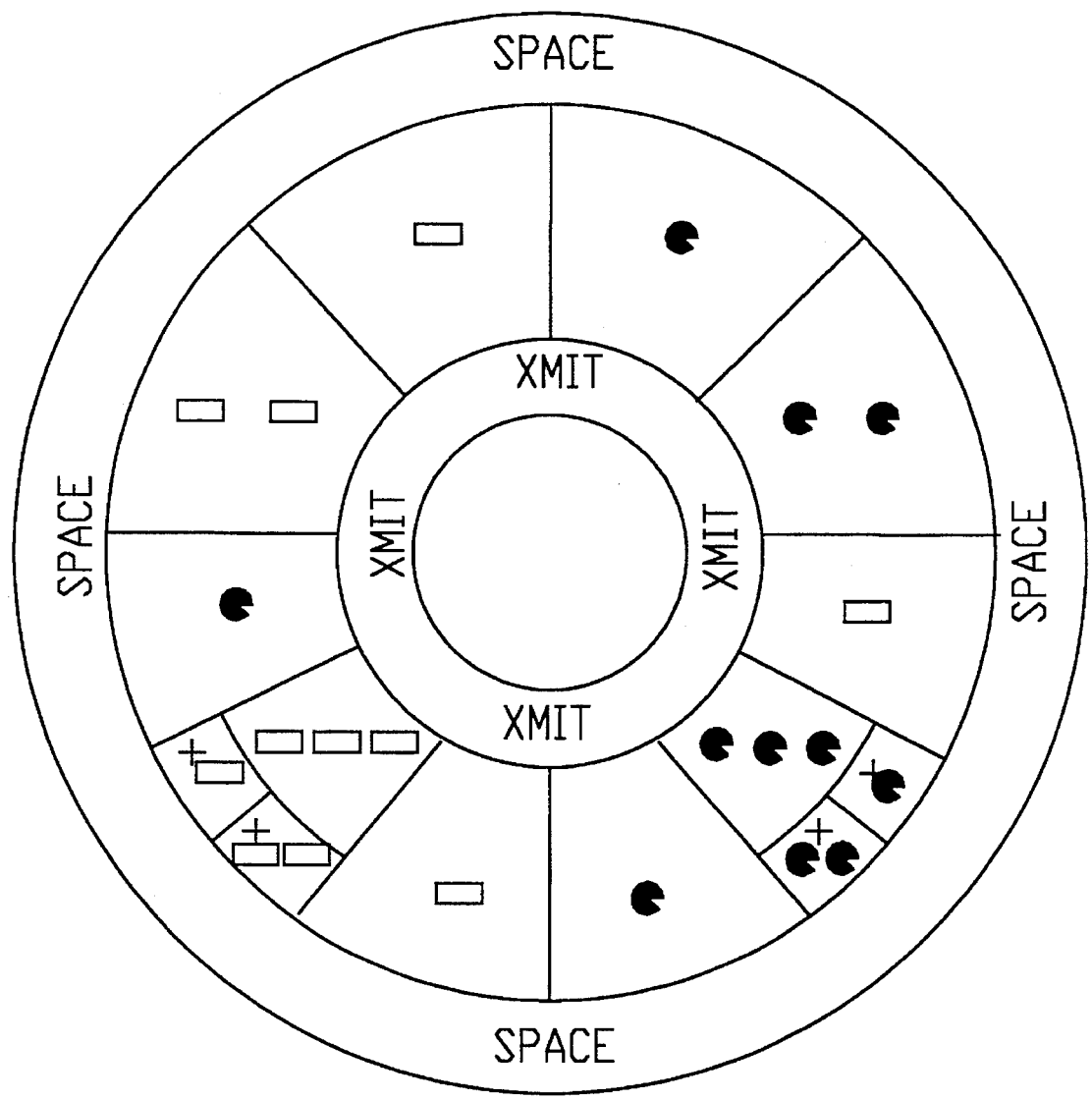

As demonstrated, this seek-and-select procedure in a word processing application is repeated, to select a series of characters and spaces in succession until the desired word is spelled out. Many other applications provide a portfolio of other utility which can include similar seek and select sequences. For example, a "Morse code wheel," as illustrated in FIG. 19B, can be operated in a manner similar to the word processing sequence. The "wheel" screen is comprised of sectors, wherein each sector represents one or more dots and dashes. To encode a series of characters, the user "seeks-and-selects" different dot or dash patterns, by moving the cursor from one sector to another to encode one or more alphanumeric characters. The user continues to select character encoding sequences to spell words. Spaces between words are selected, as needed. When the user reaches the end of their desired message he/she selects the "xmit" sector, which automatically routes the encoded message train to a preselected destination.

Throughout this document, the term "transceiver" has been used to illustrate that according to the present invention, both a "transmitter" and a "receiver" are provided together in close proximity for two-way, or "duplex" operation (i.e., base transceiver 20 has both a transmitter and a receiver contained within the same electronic enclosure, as both transmission and reception of signals are provided therein). By like reasoning, the user input device 10 can also be designated as a "transceiver" given its duplex communications capability shown by "kill circuit" and other "receiver" functions.

Although specific embodiments are specifically illustrated and described herein, it will be apparent that many modifications and variations of the present invention are possible in light of the above teachings and within the purview of the appended claims without departing from the spirit and intended scope of the invention.

What is claimed is:

1. A method of interfacing a user with a at least one computer, comprising the steps of:
   operating a plurality of discrete switches on a user interface device with one of a single finger and a thumb, wherein said user interface device is attached to a different single finger of a user than the finger or thumb which operates the device, and wherein said switches are operable by at least one finger tip of such user;
   generating computer control signals by performing said operating step;
   transmitting said computer control signals through at least one communications channel;
   receiving said transmitted computer control signals in a base computer interface device;
   decoding said transmitted signals;
   relaying said decoded signals to said at least one computer such that said at least one computer is controlled by said user interface device; and
   controlling operation of said at least one computer in response to said decoded signals.

2. The method of claim 1, further comprising the step of controlling a display connected to a respective one of said at least one computer in response to said decoded signals.

3. The method of claim 1 wherein said operating switches are operable by a thumb tip.

4. A user and computer interface system, comprising:
   an ergonomically shaped single finger attached interface means for generating computer control signals by at least one computer user, wherein said computer control signals are organized in message packets and wherein said interface means is operable by a single finger other than the finger to which said interface means is mounted;
   coding means for encoding said message packets in a format suitable for transmission;
   signal transmission means for transmitting said coded message packets, said signal transmission means including at least one communication channel;
   detecting means for detecting said coded message packets;
   conversion means for converting said coded message packets detected by said detecting means into computer processible signals; and
   relaying means for relaying said computer processible signals into at least one computer, wherein said at least one computer is adapted for processing and responding to said computer processible signals;
   said interface means including a plurality of discrete switches operable by one of the user's finger and thumb.

5. The system of claim 4 wherein said at least one computer includes a graphic user interface means for providing graphical information on a display means and for allowing said at least one user to select and control at least part of said graphical information.

6. The system of claim 4, further comprising display means for displaying images generated by said at least one computer in response to said computer processible signals.

7. The system of claim 4, further comprising a keypad means for entering user passwords and for enabling at least one enterprise resource connected to said at least one computer wherein said enterprise resource is at lest one of said detecting means, said conversion means, said computer, or said user interface means.

8. The system of claim 4, wherein said interface means further comprises means for importing and exporting data.

9. The system of claim 4, wherein said interface means includes manually operable element means for generating said computer control signals by said at least one computer user.

10. The system of claim 10, wherein said interface means includes at least one switch means for initiating generation of different computer control signals by said at least one computer user based upon a position of said at least one switch means.

11. The system of claim 10, wherein said interface means further includes mode switch means for changing said computer control signals based upon a position of said mode switch means and said at least one switch means.

12. The system of claim 4, wherein said detecting means further comprises:
kill signal transmission means for transmitting a kill signal to said interface means;
wherein said interface means includes a kill switch signal reception means for receiving said kill signal and for disabling said transmission means in response to said kill signal.

13. The system of claim wherein said interface means includes a ROM cabinet means adapted to receive at least one removably insertable ROM personality module, from which said computer control signals are originated based upon information contained in said ROM personality module.

14. The system of claim 4, wherein said interface means includes attachment means for encircling and affixing said interface means onto the proximal or medial forefinger phalange of at least one such user to permit thumb tip operation.

15. The system of claim 4 further comprising:
an ergonomically shaped enclosure means for enclosing said interface means, said coding means and said signal transmission means, wherein said enclosure means includes:
at least one contoured surface adapted for receiving the proximal or medial phalange of the forefinger of such at least one user; and
attachment means for encircling and affixing said proximal or medial forefinger phalange of such at least one user into said at least one contoured surface.

16. The system of claim 4, wherein said at least one communications channel operates using electromagnetic radiation.

17. The system of claim 4, wherein said at least one communications channel operates using infrared transmissions.

18. The system of claim 3, wherein said at least one communications channel operates using acoustic transmissions.

19. The system of claim 4, further comprising:
a power source for providing power to said interface means, including said coding means and said signal transmission means; and
charging means for charging said power source.

20. The system of claim 19, wherein said detecting means, said conversion means and said charging means are provided in a single housing to form a base computer interface device.

21. The system of claim 11, wherein said at least one switch means includes at least one thumb switch located so as to be easily operable by a user's thumb tip when said interface means is attached to the user's forefinger.

22. The system of claim 21, wherein said at least one switch means further includes a second switch opposite said thumb switch so as to be easily operable by said user's other forefinger.

23. The system of claim 20 wherein said power source means is a replaceable battery.

24. The system of claim 4, wherein said single finger attached interface means is capable of being attached to any one of a user's index or forefinger.

25. An electronic interface enclosure adapted for communication with at least one computer, comprising:
single finger attaching means to permit attachment of said electronic interface enclosure to a user's single finger in order to permit desk-free and keyboard-free operability, wherein said electronic interface enclosure is operable by a finger other than the finger to which the electronic interface enclosure is attached, said electronic interface enclosure further comprising:
at least one contoured surface of said electronic interface enclosure for receiving a finger of said user's hand;
signal generating means for generating signals wherein said signals include user initiated computer control signals;
coding means for encoding said user initiated computer control signals in the form of message packets;
signal transmission means for transmitting said message packets in a format suitable for transmission and detection; and
a plurality of discrete switches operable by one of the user's finger and thumb.

26. The electronic interface enclosure of claim 25, wherein said finger attaching means further comprises at least one strap.

27. The electronic interface enclosure of claim 25, wherein said attaching means is attachable onto the proximal or medial forefinger phalange of at least one such user to permit thumb tip operation.

28. An electronic interface enclosure comprising:
single finger attaching means for attaching said electronic interface enclosure to a user's single finger to permit desk-free and keyboard-free operability;
signal generating means for generating signals wherein said signals include user initiated computer control signals;
coding means for encoding said user initiated computer control signals in the form of message packets;
signal transmission means for transmitting said message packets in a format suitable for transmission and detection;
signal detection means for detecting externally originated coded signals, including a kill signal;
conversion means for converting said detected externally originated coded signals into microprocessor processible signals; and
responding means for responding to said microprocessor processible signals;
said signal generating means including a plurality of discrete switches operable by one of the user's finger, other than said user's single finger, and thumb.

29. The electronic interface enclosure of claim 28 wherein said single finger attaching means provides means for ambidextrous attachment of said electronic interface enclosure on to either of a user's hands to permit left-handed operation, right-handed operation or operation by physically impaired users.

30. The system of claim 28 wherein said electronic enclosure further comprises at least one contoured surface and strapping means to permit secure attachment and comfortable fit of said electronic interface enclosure on to either a left-hand or a right-hand.

31. The system of claim 28 wherein said electronic enclosure further comprises at least two contoured surfaces and a bilaterally attachable strapping means for ensuring comfortable fit of said electronic interface enclosure on to either a left-hand or a right-hand.

32. The system of claim 28 wherein said electronic interface enclosure is adapted for control of a computer using a graphic user interface, and wherein said electronic interface enclosure permits operation of said computer using said graphic user interface.

33. The system of claim 28 further comprising:
   a detector for detecting externally originated bursts of coded signals; and
   responding means for responding to said externally originated signals, said detector further including conversion means for converting said externally originated bursts of coded signals received by said detector into microprocessor processible signals.

34. The system of claim 28 wherein said responding means further comprises a kill switch for disabling said electronic interface enclosure.

35. The system of claim 28 wherein said enclosure is adapted to receive different removably insertable ROM devices for implementing different fundamental operating environment means for remote control of at least one controllable computer.

36. The system of claim 28 wherein said enclosure is adapted to receive different removably insertable ROM devices for implementing different fundamental operating environments for remote control of machinery.

37. The system of claim 28 wherein said enclosure is adapted to transmit user initiated computer control signals from a computer user to a controllable computer and wherein said enclosure is further adapted to receive externally originated signals including a kill signal.

38. The system of claim 28 wherein said enclosure is adapted to transmit user initiated computer control signals from a computer user to a controllable computer and alternatively wherein said enclosure is further adapted to transmit user initiated remote control signals for remote control of machinery by means of different removably insertable ROM devices.

39. The electronic interface enclosure means of claim 28 wherein said enclosure is adapted to transmit user initiated computer control signals from a computer user to a controllable computer and wherein said enclosure is further adapted for receiving, processing, and responding to externally originated signals, and wherein said enclosure is further adapted to transmit user initiated remote control signals for remote control and operation of machinery and is yet further adapted for receiving, processing, and responding to said externally originated signals by means of different removably insertable ROM device means.

40. The system of claim 39 wherein said responding means includes a kill switch.

41. The electronic interface enclosure of claim 28 wherein said single finger attaching means is attached onto the proximal or medial forefinger phalange of at least one such user to permit thumb tip operation.

* * * * *